United States Patent
Chester et al.

(10) Patent No.: US 10,156,031 B2
(45) Date of Patent: Dec. 18, 2018

(54) EXTENSIBLE NONWOVEN FABRIC

(71) Applicants: Fitesa Nonwoven, Inc., Simpsonville, SC (US); Fitesa Germany GmbH, Peine (DE)

(72) Inventors: Stephen O. Chester, Simpsonville, SC (US); Albert Witarsa, Camas, WA (US); Stefanie Streich, Edemissen (DE); Helmut Hartl, Braunschweig (DE); Harald Siebner, Braunschweig (DE); Daniel Kong, Simpsonville, SC (US); David D. Newkirk, Greer, SC (US)

(73) Assignees: FITESA GERMANY GMBH, Peine (DE); FITESA NONWOVEN, INC., Simpsonville, SC (US)

( * ) Notice: Subject to any disclaimer, the term of this patent is extended or adjusted under 35 U.S.C. 154(b) by 579 days.

(21) Appl. No.: 14/804,458

(22) Filed: Jul. 21, 2015

(65) Prior Publication Data

US 2015/0322605 A1    Nov. 12, 2015

Related U.S. Application Data

(63) Continuation of application No. 14/206,699, filed on Mar. 12, 2014.
(Continued)

(51) Int. Cl.
*D04H 3/147* (2012.01)
*A61L 15/24* (2006.01)
(Continued)

(52) U.S. Cl.
CPC ....... *D04H 3/147* (2013.01); *A61F 13/15658* (2013.01); *A61F 13/15707* (2013.01);
(Continued)

(58) Field of Classification Search
CPC .......... A61F 13/15658; A61F 13/15707; A61F 13/539; A61F 2013/5395; Y10T 442/641;
(Continued)

(56) References Cited

U.S. PATENT DOCUMENTS 3,338,992 A    8/1967    Kinney
3,692,613 A    9/1972    Pederson
(Continued)

FOREIGN PATENT DOCUMENTS

CN    1181429 A    5/1998
CN    1222588 A    7/1999
(Continued)

OTHER PUBLICATIONS

Office Action for European Patent Application No. 14717309.0 dated Jul. 19, 2017, 4 pages.
(Continued)

*Primary Examiner* — Jacqueline Stephens
(74) *Attorney, Agent, or Firm* — Alston & Bird LLP

(57) ABSTRACT

Extensible nonwoven fabrics having improved elongation, extensibility, abrasion resistance and toughness. In particular, embodiments of the invention are directed to extensible spunbond fabrics comprising a polymeric blend of a metallocene catalyzed polypropylene, polyethylene, and a third polymer component.

11 Claims, 12 Drawing Sheets

Related U.S. Application Data

(60) Provisional application No. 61/777,791, filed on Mar. 12, 2013.

(51) Int. Cl.

| | | |
|---|---|---|
| *D04H 3/05* | (2006.01) | |
| *D04H 1/56* | (2006.01) | |
| *A61F 13/539* | (2006.01) | |
| *A61F 13/15* | (2006.01) | |
| *D04H 1/4291* | (2012.01) | |
| *D04H 1/541* | (2012.01) | |
| *D04H 1/544* | (2012.01) | |
| *D04H 3/007* | (2012.01) | |
| *D04H 5/06* | (2006.01) | |

(52) U.S. Cl.
CPC ............ *A61F 13/539* (2013.01); *A61L 15/24* (2013.01); *D04H 1/4291* (2013.01); *D04H 1/541* (2013.01); *D04H 1/544* (2013.01); *D04H 1/56* (2013.01); *D04H 3/007* (2013.01); *D04H 3/05* (2013.01); *D04H 5/06* (2013.01); *A61F 2013/5395* (2013.01); *D10B 2321/021* (2013.01); *D10B 2321/022* (2013.01); *D10B 2401/06* (2013.01); *D10B 2509/026* (2013.01); *Y10T 442/641* (2015.04); *Y10T 442/66* (2015.04); *Y10T 442/681* (2015.04); *Y10T 442/697* (2015.04)

(58) Field of Classification Search
CPC ............... Y10T 442/66; Y10T 442/681; Y10T 442/697; D04H 3/147; D04H 3/007; D04H 3/05; D04H 1/4291; D04H 1/541; D04H 1/544; D04H 1/56; D10B 2321/021; D10B 2321/022; D10B 2401/06; D10B 2509/026
See application file for complete search history.

(56) References Cited

U.S. PATENT DOCUMENTS

| | | |
|---|---|---|
| 3,802,817 A | 4/1974 | Matsuki et al. |
| 3,849,241 A | 11/1974 | Butin et al. |
| 4,223,059 A | 9/1980 | Schwarz |
| 4,405,297 A | 9/1983 | Appel et al. |
| 4,657,802 A | 4/1987 | Morman |
| 4,789,592 A | 12/1988 | Taniguchi et al. |
| 4,795,668 A | 1/1989 | Krueger et al. |
| 4,863,779 A | 9/1989 | Daponte |
| 5,057,368 A | 10/1991 | Largman et al. |
| 5,069,970 A | 12/1991 | Largman et al. |
| 5,108,820 A | 4/1992 | Kaneko et al. |
| 5,162,074 A | 11/1992 | Hills |
| 5,169,706 A | 12/1992 | Collier, IV et al. |
| 5,277,976 A | 1/1994 | Hogle et al. |
| 5,336,552 A | 8/1994 | Strack et al. |
| 5,344,297 A | 9/1994 | Hills |
| 5,382,400 A | 1/1995 | Pike et al. |
| 5,466,410 A | 11/1995 | Hills |
| 5,545,464 A | 8/1996 | Stokes |
| 5,665,300 A | 9/1997 | Brignola et al. |
| 5,744,548 A | 4/1998 | Nohr et al. |
| 5,804,286 A | 9/1998 | Quantrille et al. |
| 5,804,517 A | 9/1998 | Ishii et al. |
| 5,814,349 A | 9/1998 | Geus et al. |
| 5,908,594 A | 6/1999 | Gownder et al. |
| 6,200,669 B1 | 3/2001 | Marmon et al. |
| 6,344,102 B1 | 2/2002 | Wagner |
| 6,417,121 B1 | 7/2002 | Newkirk et al. |
| 6,420,285 B1 | 7/2002 | Newkirk et al. |
| 6,476,135 B1 | 11/2002 | Bugada et al. |
| 6,506,698 B1 | 1/2003 | Quantrille et al. |
| 6,649,548 B1 | 11/2003 | Shawver et al. |
| 6,737,009 B2 | 5/2004 | Taylor et al. |
| 6,845,134 B2 | 1/2005 | Stek et al. |
| 6,908,292 B2 | 6/2005 | Geus et al. |
| 6,994,763 B2 | 2/2006 | Austin |
| 7,319,077 B2 | 1/2008 | Mehta et al. |
| 7,319,122 B2 | 1/2008 | Cheng et al. |
| 7,491,770 B2 | 2/2009 | Autran et al. |
| 7,619,038 B2 | 11/2009 | Mehta et al. |
| 7,781,527 B2 | 8/2010 | Autran et al. |
| 7,960,478 B2 | 6/2011 | Autran et al. |
| 7,998,579 B2 | 8/2011 | Lin et al. |
| 8,093,162 B2 | 1/2012 | Hartl et al. |
| 8,168,853 B2 | 5/2012 | Autran et al. |
| 8,198,200 B2 | 6/2012 | Autran et al. |
| 8,211,968 B2 | 7/2012 | Yang et al. |
| 8,226,626 B2 | 7/2012 | Turner et al. |
| 8,231,595 B2 | 7/2012 | Turner et al. |
| 8,388,594 B2 | 3/2013 | Turner et al. |
| 8,454,780 B2 | 6/2013 | Anderson et al. |
| 8,586,490 B2 | 11/2013 | Autran et al. |
| 2002/0019490 A1 | 2/2002 | Maugans et al. |
| 2005/0164586 A1 | 7/2005 | Autran et al. |
| 2005/0165173 A1 | 7/2005 | Autran et al. |
| 2005/0182198 A1 | 8/2005 | Cheng et al. |
| 2006/0183860 A1 | 8/2006 | Mehta et al. |
| 2008/0160862 A1 | 7/2008 | Sartori et al. |
| 2008/0172840 A1 | 7/2008 | Kacker et al. |
| 2009/0143536 A1 | 6/2009 | Autran et al. |
| 2010/0041293 A1 | 2/2010 | Anderson et al. |
| 2010/0228214 A1 | 9/2010 | Bornemann et al. |
| 2010/0233927 A1 | 9/2010 | Standaert et al. |
| 2010/0286339 A1 | 11/2010 | Autran et al. |
| 2011/0040040 A1 | 2/2011 | Bornemann et al. |
| 2011/0144608 A1* | 6/2011 | Kim .................. D04H 3/14 604/367 |
| 2012/0108714 A1 | 5/2012 | Wittner |
| 2013/0237938 A1 | 9/2013 | Autran et al. |
| 2014/0018758 A1 | 1/2014 | Jayasinghe et al. |
| 2014/0018759 A1 | 1/2014 | Jayasinghe et al. |

FOREIGN PATENT DOCUMENTS

| | | |
|---|---|---|
| CN | 1922262 A | 2/2007 |
| CN | 101821330 A | 9/2010 |
| CN | 101842526 A | 9/2010 |
| EP | 0 740 714 A1 | 11/1996 |
| EP | 0 815 305 A1 | 1/1998 |
| EP | 0 924 322 A1 | 6/1999 |
| EP | 1 264 017 A2 | 12/2002 |
| EP | 2 034 056 A1 | 3/2009 |
| EP | 2 270 271 A1 | 1/2011 |
| EP | 2 463 413 A1 | 6/2012 |
| JP | H10266056 A | 10/1998 |
| JP | H11-181620 A | 7/1999 |
| JP | H11-241224 A | 9/1999 |
| JP | 2002-529616 A | 9/2002 |
| JP | 2002-531721 A | 9/2002 |
| JP | 2007-522284 A | 8/2007 |
| JP | 2008-524387 A | 7/2008 |
| JP | 2012-251254 A | 12/2012 |
| WO | WO 96/16216 A1 | 5/1996 |
| WO | WO 00/028122 A1 | 5/2000 |
| WO | WO 00/34385 A1 | 6/2000 |
| WO | WO 2005/0073309 A1 | 8/2005 |
| WO | WO 2006/065648 A1 | 6/2006 |
| WO | WO 2010/149239 A1 | 12/2010 |
| WO | WO 2011/088106 A2 | 7/2011 |
| WO | WO 2012/055797 A1 | 5/2012 |

OTHER PUBLICATIONS

Office Action for Japanese Patent Application No. 2016-501677 dated Dec. 5, 2017 with English translation, 10 pages.
Office Action for Chinese Patent Application No. 201480027245.1 dated Oct. 30, 2017 with English Translation, 19 pages.
Office Action for Japanese Patent Application No. 2016-501677 dated Dec. 27, 2016.

(56) References Cited

OTHER PUBLICATIONS

Office Action for Chinese Patent Application No. 201480027245.1 dated Nov. 30, 2016
Office Action for European Patent Application No. 14717309.0 dated Mar. 17, 2017, 5 pages.
Kaminsky, W., *Highly Active Metallocene Catalysts for Olefin Polymerization*, J. Chem. Soc., Dalton Trans. (1998) 1413-1418.
Kaminsky, W., *The Discovery of Metallocene Catalysts and Their Present State of the Art*, Journal of Polymer Science: Part A; Polymer Chemistry, vol. 42 (2004) 3911-3921.
U.S. Appl. No. 60/763,543, filed Jan. 31, 2006; In re: Abed et al., entitled *Apparatus and Method for Stretching an Extensible Sheet Material*.
International Search Report and Written Opinion for Application No. PCT/US2014/024907 dated Jun. 26, 2014.

\* cited by examiner

EXTENSIBLE NONWOVEN FABRIC

CROSS REFERENCE TO RELATED APPLICATION

This application is a continuation of U.S. application Ser. No. 14/206,699 filed Mar. 12, 2014, which claims priority to U.S. Provisional Application No. 61/777,791, filed Mar. 12, 2013, the entire disclosure of which is hereby incorporated herein by reference.

FIELD

The present invention relates to composite nonwoven fabrics, and more particularly to extensible nonwoven fabrics which are capable of elongation via mechanical stretching.

BACKGROUND

Nonwoven fabrics are used in a variety of applications such as garments, disposable medical products, diapers and personal hygiene products. New products being developed for these applications have demanding performance requirements, including comfort, conformability to the body, freedom of body movement, good softness and drape, adequate tensile strength and durability, and resistance to surface abrasion, pilling or fuzzing. Accordingly, the nonwoven fabrics which are used in these types of products must be engineered to meet these performance requirements.

One such type of nonwoven fabric includes fabrics that include elasticity. One approach which has been taken to providing such elastic properties in a composite nonwoven fabric involves forming and stretching an elastic web, then bonding a gatherable web to the elastic web, and relaxing the composite. An obvious limitation of this approach is having to form the composite in the tensioned state. This requires additional equipment and control systems. Examples of this process are Mormon, U.S. Pat. No. 4,657,802, where it is disclosed that a composite nonwoven elastic is made by first stretching an elastic web, forming a fibrous nonwoven gatherable web onto the stretched elastic nonwoven, joining the two together to form a composite structure, then allowing the composite to relax. In Collier, et al., U.S. Pat. No. 5,169,706, it is disclosed that a composite elastic material having a low stress relaxation is formed between an elastic sheet and a gatherable layer. In Daponte, U.S. Pat. No. 4,863,779, a composite is disclosed which involves first tensioning the elastic web to elongate it, bonding at least one gatherable web to the elastic web, and relaxing the composite immediately after bonding, so that the gatherable web is gathered between the bond points.

Another approach to imparting elastic properties to a composite nonwoven fabric is with a so-called "zero-strain" stretchable laminate. A "zero-strain" stretchable laminate refers to a fabric in which at least two layers of material, one elastic, the other substantially inelastic, are secured to one another along their coextensive surfaces while in a substantially untensioned state. The fabric is subsequently subjected to mechanical stretching. The inelastic layer typically fractures or extends, thus permanently elongating the inelastic layer and producing a composite fabric with elastic properties. This lamination and stretching process is advantageous in that utilizing elastic in an unstretched condition is easier and less expensive than stretched elastic used in traditional processing operations. However, one problem which has existed with presently available "zero-strain" stretchable laminates is surface abrasion. The mechanical stretching either fractures or disrupts the fibers within the substantially inelastic component of the "zero-strain" laminate, and as a result, the fibers detach and are susceptible to linting and pilling. In addition, such fracturing or detachment causes a noticeable loss in fabric strength.

Another technique involves the use of extensible nonwoven fabrics that are elongated by application of a tensile stretching force. However, it has been found that fibers having good extensibility without sacrificing drapeability and abrasion resistant are difficult to produce. Accordingly, there still exists a need for highly extensible fabrics with improved feel and abrasion resistance.

BRIEF SUMMARY OF THE INVENTION

Embodiments of the present invention are directed to nonwoven fabrics having improved elongation, extensibility, abrasion resistance and toughness. In particular, embodiments of the invention are directed to extensible spunbond fabrics comprising a polymeric blend of a metallocene catalyzed polypropylene, polyethylene, and a third polymer component.

The inventors of the present invention have surprisingly discovered that nonwoven fabrics of the present invention have improved elongation and toughness in comparison to nonwoven fabrics comprising a blend of Ziegler-Natta catalyzed polypropylene, polyethylene, and a third polymer component. Hence, nonwoven fabrics of the present invention may be particularly useful in applications where high extensibility is desirable. In particular, embodiments of the invention provide a nonwoven fabric comprising a plurality of fibers that are bonded together to form a coherent web, wherein the fibers comprise a polymeric blend of a metallocene catalyzed polypropylene component, a polyethylene component, and a third polymer component that is at least partially miscible in the metallocene catalyzed polypropylene component and polyethylene component. Advantageously, the nonwoven fabric exhibits a 5 to 40% improvement in one or more of a cross direction or machine direction peak elongation in comparison to a similar or identical nonwoven fabric comprising a Ziegler-Natta catalyzed polypropylene in place of the metallocene catalyzed polypropylene.

In addition, nonwoven fabrics of the present invention may exhibit improvements in strength, softness, and abrasion resistant. Nonwoven fabrics of the present invention are also compatible with solid state modification processes, such as ring rolling.

In one embodiment, the present invention is directed to a highly extensible spunbond nonwoven fabric having filaments that are thermally bonded to each other to provide a coherent web. In one embodiment, the filaments are bonded via point bonding. For example, the nonwoven fabric may include a bond area ranging from about 6 to 40% of the nonwoven surface, and in particular, from about 8 to 25%, and more particularly, from about 8 to 20%.

Nonwoven fabrics in accordance with some embodiments of the present invention may include bond patterns having rod shapes that extend in the cross direction of the fabric, or elliptical (oval) shaped bonding patterns.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION OF THE INVENTION

Figure 1:
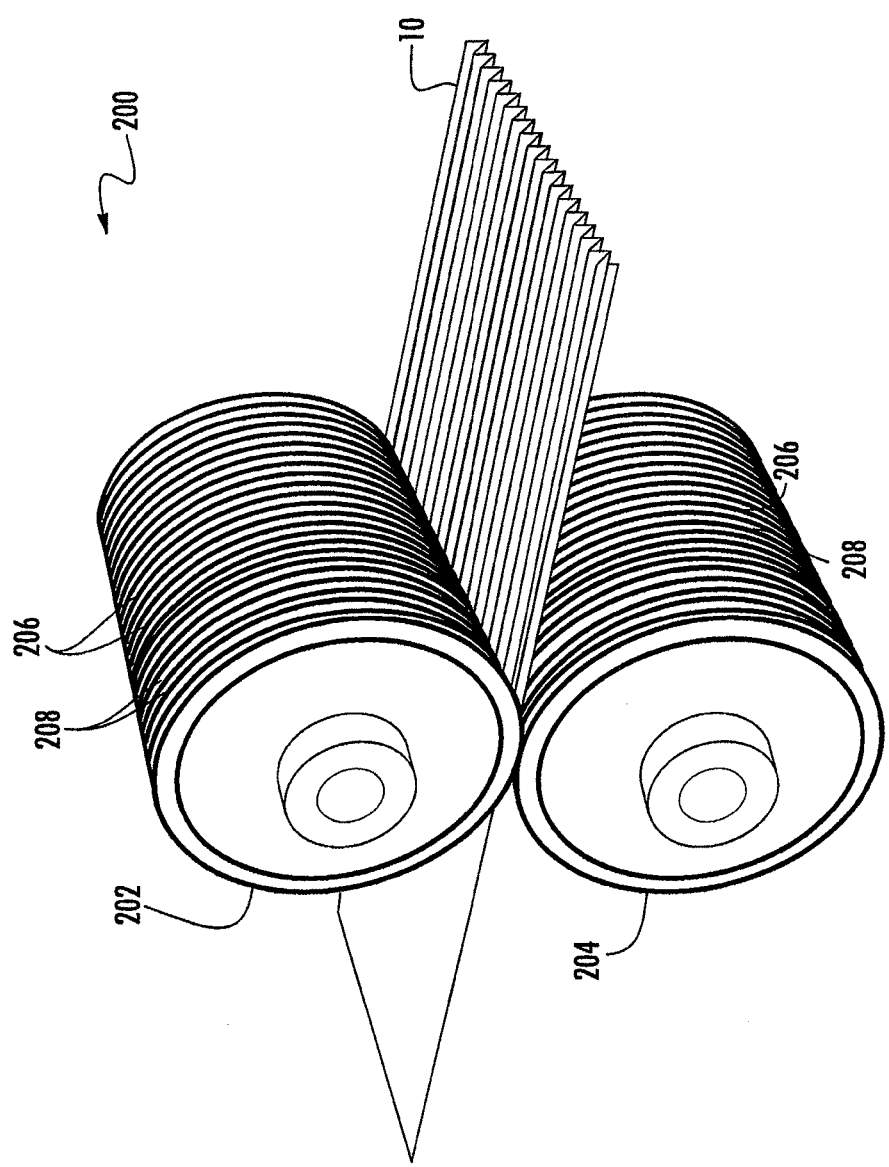
FIG. 1 illustrates an incremental stretching system in accordance with one aspect of the present invention.
Figure 2:
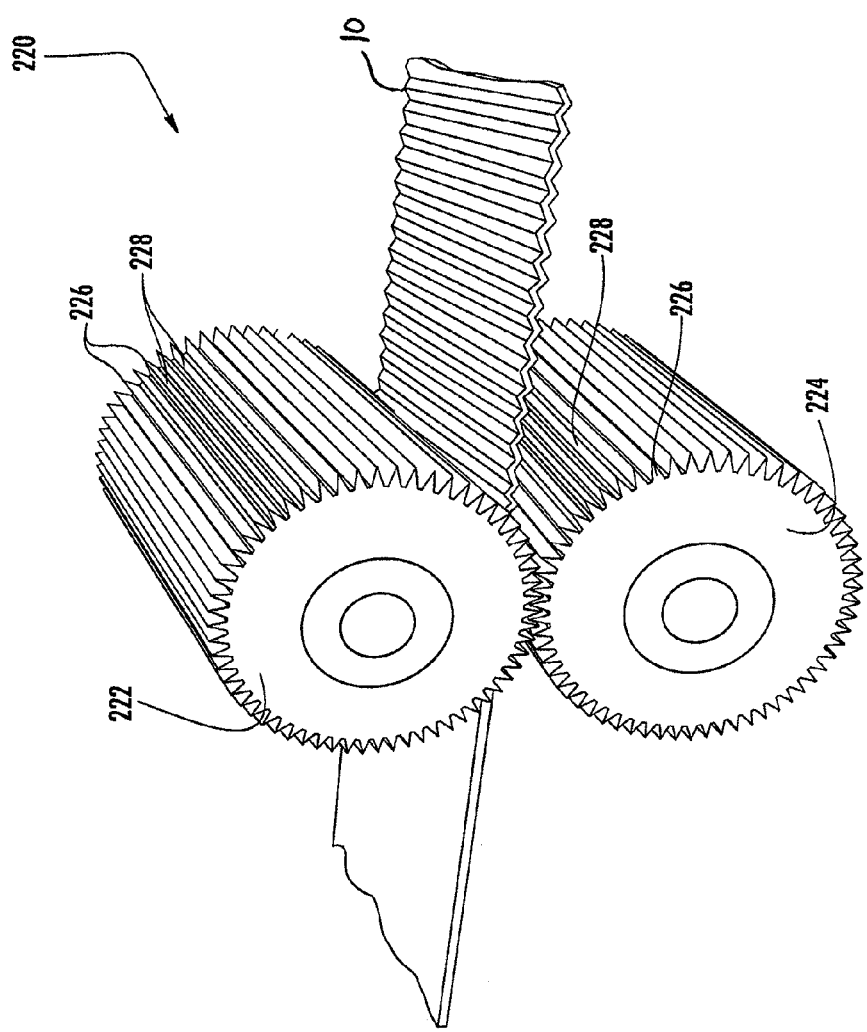
FIG. 2 illustrates an incremental stretching system in accordance with another aspect of the present invention.

The present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

For the purposes of the present application, the following terms shall have the following meanings:

The term "fiber" can refer to a fiber of finite length or a filament of infinite length.

As used herein, the term "monocomponent" refers to fibers formed from one polymer or formed from a single blend of polymers. Of course, this does not exclude fibers to which additives have been added for color, anti-static properties, lubrication, hydrophilicity, liquid repellency, etc.

As used herein, the term "multicomponent" refers to fibers formed from at least two polymers (e.g., bicomponent fibers) that are extruded from separate extruders. The at least two polymers can each independently be the same or different from each other, or be a blend of polymers. The polymers are arranged in substantially constantly positioned distinct zones across the cross-section of the fibers. The components may be arranged in any desired configuration, such as sheath-core, side-by-side, pie, island-in-the-sea, and so forth. Various methods for forming multicomponent fibers are described in U.S. Pat. No. 4,789,592 to Taniguchi et al. and U.S. Pat. No. 5,336,552 to Strack et al., U.S. Pat. No. 5,108,820 to Kaneko, et al., U.S. Pat. No. 4,795,668 to Kruege, et al., U.S. Pat. No. 5,382,400 to Pike, et al., U.S. Pat. No. 5,336,552 to Strack, et al., and U.S. Pat. No. 6,200,669 to Marmon, et al., which are incorporated herein in their entirety by reference. Multicomponent fibers having various irregular shapes may also be formed, such as described in U.S. Pat. No. 5,277,976 to Hogle, et al., U.S. Pat. No. 5,162,074 to Hills, U.S. Pat. No. 5,466,410 to Hills, U.S. Pat. No. 5,069,970 to Largman, et al., and U.S. Pat. No. 5,057,368 to Largman, et al., which are incorporated herein in their entirety by reference.

As used herein the terms "nonwoven," "nonwoven web" and "nonwoven fabric" refer to a structure or a web of material which has been formed without use of weaving or knitting processes to produce a structure of individual fibers or threads which are intermeshed, but not in an identifiable, repeating manner. Nonwoven webs have been, in the past, formed by a variety of conventional processes such as, for example, meltblown processes, spunbond processes, and staple fiber carding processes.

As used herein, the term "meltblown" refers to a process in which fibers are formed by extruding a molten thermoplastic material through a plurality of fine, usually circular, die capillaries into a high velocity gas (e.g. air) stream which attenuates the molten thermoplastic material and forms fibers, which can be to microfiber diameter. Thereafter, the meltblown fibers are carried by the gas stream and are deposited on a collecting surface to form a web of random meltblown fibers. Such a process is disclosed, for example, in U.S. Pat. No. 3,849,241 to Buntin et al.

As used herein, the term "machine direction" or "MD" refers to the direction of travel of the nonwoven web during manufacturing.

As used herein, the term "cross direction" or "CD" refers to a direction that is perpendicular to the machine direction and extends laterally across the width of the nonwoven web.

As used herein, the term "spunbond" refers to a process involving extruding a molten thermoplastic material as filaments from a plurality of fine, usually circular, capillaries of a spinneret, with the filaments then being attenuated and drawn mechanically or pneumatically. The filaments are deposited on a collecting surface to form a web of randomly arranged substantially continuous filaments which can thereafter be bonded together to form a coherent nonwoven fabric. The production of spunbond non-woven webs is illustrated in patents such as, for example, U.S. Pat. Nos. 3,338,992; 3,692,613, 3,802,817; 4,405,297 and 5,665,300. In general, these spunbond processes include extruding the filaments from a spinneret, quenching the filaments with a flow of air to hasten the solidification of the molten filaments, attenuating the filaments by applying a draw tension, either by pneumatically entraining the filaments in an air stream or mechanically by wrapping them around mechanical draw rolls, depositing the drawn filaments onto a foraminous collection surface to form a web, and bonding the web of loose filaments into a nonwoven fabric. The bonding can be any thermal or chemical bonding treatment, with thermal point bonding being typical.

As used herein "thermal point bonding" involves passing a material such as one or more webs of fibers to be bonded between a heated calender roll and an anvil roll. The calender roll is typically patterned so that the fabric is bonded in discrete point bond sites rather than being bonded across its entire surface.

As used herein the term, "high speed deformation" refers to processes where a nonwoven is stretched rapidly such as for example during ring rolling. Such processes may operate at strain rates of greater than 200 reciprocal seconds (Autran et al., U.S. Pat. No. 7,960,478).

As used herein the term "polymer" generally includes, but is not limited to, homopolymers, copolymers, such as, for example, block, graft, random and alternating copolymers, terpolymers, etc. and blends and modifications thereof. Furthermore, unless otherwise specifically limited, the term "polymer" shall include all possible geometrical configurations of the material, including isotactic, syndiotactic and random symmetries.

The term "extensible", as used herein, means a material which, upon application of a tensile stretching force, becomes permanently elongated. A practical test for extensibility can be carried out using the incremental stretching apparatus described in FIG. 7. If a fabric can be elongated 150% beyond its original length in this apparatus without breaking, then it is extensible. After its removal from the incremental stretching apparatus, the fabric may exhibit at least a 15% reduction in its basis weight.

The terms "recover" and "recovery" as used herein refer to a contraction of a stretched material upon release of the tensile stretching force. The extensible materials suitable for the present invention have recoveries of less than 50% when elongated to an extension of 150% or greater in a standard laboratory tensile tester such as an Instron, and in particular, less than about 40%, less than about 30%, less than about 25%, less than about 20%, less than about 15%, and less than about 10%.

The term "extensible inelastic" as used herein, means a material which, upon application of a tensile stretching force, can be stretched beyond its elastic limit and becomes permanently elongated. The material has little retractive force and is therefore inelastic. Generally, extensible inelastic materials are substantially inelastic and recover less than about 5% of their pre-elongated dimensions upon release of a tensile stretching force.

The term "incremental stretching" as used herein refers to a process in which a web is supported at closely spaced apart locations and then the unsupported segments of the web between these closely spaced apart locations are stretched. This can be accomplished by passing the web through a nip formed between a pair of meshing corrugated rolls, which have an axis of rotation perpendicular to the direction of web travel. Incremental stretching rolls designed for machine direction and cross direction stretching are described in U.S. Pat. No. 4,223,059, incorporated herein by reference. Another type of incremental stretching apparatus is described in U.S. Pat. No. 6,344,102 where one of the rolls includes a plurality of projections and the other roll includes blades that are received between the projections so that the web is incrementally stretched by deep embossing.

As used herein, the term "activated" refers to a material which has been mechanically deformed in order to increase the extensibility of at least a portion of the material. A material may be activated by, for example, incrementally stretching the material in at least one direction.

Polymeric Blend

A first aspect of the present invention is directed to an extensible nonwoven web comprising a plurality of fibers that include a polymeric blend of a metallocene catalyzed polypropylene polymer component, a polyethylene polymer component, and a third polymer component, such as a propylene copolymers and terpolymers. In one embodiment, the present invention is directed to nonwoven webs comprised of fibers having improved extensibility upon application of a stretching tensile force. The inventors of the present invention have surprisingly discovered that polymeric blends including a metallocene catalyzed polypropylene component can be used to prepare extensible nonwoven fabrics having improved elongation in comparison to a nonwoven fabric comprised of fibers composed of a blend of a Ziegler-Natta polypropylene, polyethylene, and a third polymer component. In particular, nonwoven webs comprising a polymeric blend of a metallocene catalyzed polypropylene polymer component, a polyethylene polymer component, and a third polymer component have shown the following improvements in elongation in comparison to a similar fabric having a Ziegler-Natta catalyzed polypropylene as set forth below.

| | | | | |
|---|---|---|---|---|
| Increase in MD peak elongation in comparison to a fabric having Ziegler-Natta catalyzed polypropylene | about 5-40% | about 10-40% | about 10-30% | about 15-30% |
| Increase in CD peak elongation in comparison to a fabric having Ziegler-Natta catalyzed polypropylene | about 5-40% | about 10-40% | about 10-30% | about 15-30% |
| Increase in MD elongation at 5N in comparison to a fabric having Ziegler-Natta catalyzed polypropylene | about 5-40% | about 10-30% | about 10-25% | about 15-25% |
| Increase in CD elongation at 5N in comparison to a fabric having Ziegler-Natta catalyzed polypropylene | about 5-40% | about 10-30% | about 10-25% | about 15-25% |
| Increase in MD elongation at 10 Nin comparison to a fabric having Ziegler-Natta catalyzed polypropylene | about 20-80% | about 25-70% | about 30-70% | about 30-60% |
| Increase in CD elongation at 10 Nin comparison to a fabric having Ziegler-Natta catalyzed polypropylene | about 20-80% | about 25-70% | about 30-70% | about 30-60% |

The increases in elongation percentages were calculated according to the High Speed Deformation Simulation test set forth more fully below at a speed of 200 mm/min.

U.S. Pat. Nos. 5,804,286 and 6,506,698 describe nonwoven fabrics comprising filaments composed of a blend of Ziegler-Natta polypropylene, polyethylene, and a third polymer. Although, the filaments, and resulting fabrics, are generally extensible, they have generally shown poor conversion when the fabrics are prepared using Reifenhaeuser spunbond technology.

In some embodiments, extensible nonwoven fabrics in accordance with embodiments of the invention may also exhibit root mean square peak tensile of about 10 N/5 cm or less and a root mean square peak elongation greater than 400% as measured in accordance with the High Speed Deformation Simulation at 800 mm/minute. In one embodiment, the nonwoven fabric may exhibit a root mean square peak tensile of about 5 to 10 N/5 cm, and in particular from 6 to 9 N/5 cm, and a root mean square peak elongation greater from about 400% to 600%, and in particular, from about 425 to 550% as measured in accordance with the High Speed Deformation Simulation at 800 mm/minute.

In one particular embodiment, the invention comprises a reverse bicomponent fabric having a sheath core arrangement in which the sheath comprises a first component of the polymer blend and the core comprises a second component of a polymer having a lower melting temperature than the polymer blend, and in which the fabric has a root mean square peak tensile of about 10 N/5 cm or less and a root mean square peak elongation greater than 400% as measured in accordance with the High Speed Deformation Simulation at 800 mm/minute.

Polypropylene Component

The polypropylene component in accordance with embodiments of the present invention is produced in a metallocene-catalyzed polymerization. Polypropylene resins have been manufactured using Ziegler-Natta catalysts for many years. All catalysts have reactive sites that enable them to link the individual molecules of monomers to form the polymeric chain. Ziegler-Natta catalysts have many reactive sites that are located randomly on their surface. This results in a polymer having a broad molecular weight distribution. Metallocene catalyst, on the other hand, is known as a single site catalyst and produces a polymer with a much narrower molecular weight distribution. The molecular weight distribution is typically designated by the ratio of weight average molecular weight to the number average molecular weight, or Mw/Mn. Polypropylene produced with Ziegler-Natta catalyst typically has a Mw/Mn value greater than 3.5 while metallocene catalyzed polypropylene will typically have values between 1.5-2.5. Please see a more complete discussion of metallocene polyolefins in the paper, by Walter Kaminsky "Highly active metallocene catalysts for olefin polymerization"; Journal of Polymer Science; Part A; Polymer Chemistry; Vol 42, Issue 16 (First Published on Line 9 Jul. 2004).

The melt flow rate of the metallocene catalyzed polypropylene may be of any suitable value less than the melt flow rate (MFR) of the polymeric blend provided the polymeric blend has an MFR of from about 10 g/10 minutes to about 40 g/10 minutes. In one embodiment of the present invention the MFR of the metallocene catalyzed polypropylene is from about 20 g/10 minutes to about 30 g/10 minutes. In certain embodiments, the metallocene catalyzed polypropylene exhibits a molecular weight distribution of less than about 4 and a Z-average molecular weight greater than about 300,000. Typically, the molecular weight distribution (Mw/Mn) is from about 1 to 4, and more typically from about 1.5 to 5, and even more typically from about 1.5 to 3.5.

In one embodiment, metallocene catalyzed polypropylenes in accordance with the present invention may have an average melt temperature from about 140° C. to about 160° C., more preferably from about 145° C. to about 155° C.

In one embodiment, the metallocene catalyzed polypropylene component is a copolymer formed by the polymerization of propylene and either ethylene or a $C_4$ to $C_{20}$ α-olefin, wherein the polymerization is catalyzed by a metallocene catalyst. Such copolymerization disrupts the crystallinity of the polymer with a resulting reduction in the melting point thereof. As discussed above and exemplified in the Examples (below) metallocene (i.e., a positively charged metal ion sandwiched between two negatively charged cyclopentadienyl derived anions) catalyzed polypropylenes are desirable because they unexpectantly provide improvements in elongation in comparison to Ziegler-Natta catalyzed polypropylene. Examples of suitable metallocene polypropylenes may include TOTAL® M3766 polypropylene from Total Petrochemicals USA, INC of Houston, Tex.; TOTAL® MR 2001 polypropylene from Total S.A. of Courbevoie, France; ACHIEVE® 3754 polypropylene from ExxonMobil of Houston, Tex.; ACHIEVE® 3825 polypropylene from ExxonMobil of Houston, Tex., and LUMICENE®, MR 2001 available from Total Petrochemicals.

Polyethylene Component

Various types of polyethylene may be employed in the polymeric blend of the present invention. As an example, a high density polyethylene, a branched (i.e., non-linear) low density polyethylene, or a linear low density polyethylene (LLDPE) can be utilized. Polyethylenes may be produced from any of the well-known processes, including metallocene and Ziegler-Natta catalyst systems.

In one embodiment of the invention, the polyethylene component comprises a polyethylene having a density ranging from about 0.90 to 0.97 g/cc (ASTM D-792). In particular, preferred polyethyelenes have a density value ranging from 0.93 to 0.965, and more particularly from about 0.94 to 0.965. Examples of suitable polyethylenes included ASPUN™ 6834 (a polyethylene polymer resin having a melt index of 17 g/10 min (ISO 1133) and a density of 0.95 g/cc (ASTM D-792)), available from Dow Chemical Company, and HD6908.19 (a polyethylene resin supplied by ExxonMobil having a melt index in the range of 7.5 to 9 g/10 min (ISO 1133) and a density of 0.9610 to 0.9680 g/cc (ASTM D-792)).

LLDPE may also be used in some embodiments of the present invention. LLDPE is typically produced by a catalytic solution or fluid bed process under conditions established in the art. The resulting polymers are characterized by an essentially linear backbone. Density is controlled by the level of comonomer incorporated into the otherwise linear polymer backbone. Various alpha-olefins are typically copolymerized with ethylene in producing LLDPE. The alpha-olefins which preferably have four to eight carbon atoms, are present in the polymer in an amount up to about 10 percent by weight. The most typical comonomers are butene, hexene, 4-methyl-1-pentene, and octene. In general, LLDPE can be produced such that various density and melt index properties are obtained which make the polymer well suited for melt-spinning with polypropylene. Preferably, the LLDPE should have a melt index of greater than 10, and more preferably 15 or greater for spunbonded filaments. Particularly preferred are LLDPE polymers having a density of 0.90 to 0.97 g/cc and a melt index of greater than 25. Examples of suitable commercially available linear low density polyethylene polymers include those available from Dow Chemical Company, such as ASPUN Type 6811 (27 MFR g/10 min I, density 0.923), ASPUN™ Type 6834 (17 MFR g/10 min, density of 0.95 g/cc), Dow LLDPE 2500 (55 MFR g/10 min, 0.923 density), Dow LLDPE Type 6808A (36 MFR g/10 min, 0.940 density), and the Exact series of linear low density polyethylene polymers from Exxon Chemical Company, such as Exact 2003 (31 MFR g/10 min, density 0.921).

Third Polymer Component

In addition to the metallocene catalyzed polypropylene component and polyethylene component, the polymer blends also include a third polymer component. For example, the multipolymer fibers may include a dominant amount of a propylene polymer, such as isotactic polypropylene, a small amount of a polymer having low mutual affinity with the dominant polymer, such as polyethylene, and an additional third polymer which either reduces crystallinity and/or compatibilizes the blend. In particular, the third polymer component comprises a copolymer or terpolymer that is miscible or partially miscible with both the polypropylene component and the polyethylene component. What results is a softer web, with extremely high extensibility.

Suitable additional third polymers include propylene copolymers and terpolymers such as the commercially available Adflex Z 108 S, which is a thermoplastic polyolefin manufactured using the LyondellBasell's proprietary Catalloy process, and is available from LyondellBasell Polymers. These resins are generally characterized by having the comonomer(s) exist to some degree in blocks, and wherein at least some portion of the polymer chain is miscible with one or the other, or both, dominant and dispersed polymer phases. Other suitable polymers may include REFLEX™ flexible polyolefins from Rexene. These crystallinity reducing resins are characterized as having atactic segments present in the polymer chain, such that the "tacticity" of the polymer is affected.

While not wanting to be bound to a particular theory, the inventors believe that the use of polypropylene manufactured with metallocene catalyst enhances extensibility of the fabric of the invention by 1) being less miscible with the other two components and 2) reducing the degree of molecular orientation of the fibers during the drawing process. In particular, the narrow molecular weight distribution significantly reduces the concentration of very low molecular weight polymer in the blend. It is believed that this reduces the compatibility of the polypropylene component with the other two components. In the fiber draw down process, the metallocene polypropylene has lower affinity for the other components and thus interferes with the orientation and crystallization of the blend. The resultant fibers have higher extensibility in comparison to prior art fibers.

In one embodiment, fibers according to the present invention may comprise greater than 50 percent by weight of the polypropylene polymer component, 1 to 10 percent of the polyethylene component, and 10 to 40 percent of the third polymer component. Especially preferred fibers according to this embodiment comprise a polymeric blend of 65 to 80 percent metallocene catalyzed polypropylene, 1 to 5 percent polyethylene, and 15 to 30 percent of the third polymer component wherein at least a portion of the chain is miscible with metallocene catalyzed polypropylene. In one embodiment, fibers according to this embodiment comprise a polymeric blend of 65 to 80 percent metallocene catalyzed polypropylene, 1 to 5 percent polyethylene, and 15 to 30 percent of the third polymer component.

Fibers comprising the polymeric blend of the present invention may be monocomponent or multicomponent fibers. Preferred nonwoven webs include spunbond nonwoven webs of substantially continuous filaments. Alternatively, in some embodiments of the invention the nonwoven web may be a carded nonwoven web of staple fibers.

In one aspect, the present invention provides an extensible spunbond nonwoven fabric comprised of fibers comprising the polymeric blend. According to one embodiment of the invention, the present invention provides a thermally point bonded spunbond nonwoven fabric of randomly arranged substantially continuous filaments that are comprised of the polymeric blend. The spunbond nonwoven web may be produced, for example, by the conventional spunbond process wherein molten polymer is extruded into continuous filaments which are subsequently quenched, attenuated mechanically by draw rolls or pneumatically by a high velocity fluid, and collected in random arrangement on a collecting surface. After filament collection, any thermal, chemical or mechanical bonding treatment may be used to form a bonded web such that a coherent web structure results. Preferably, the spunbond web is extensible and substantially inelastic, for example, the spunbond web has a recovery that is less than about 5%. The extensible nonwoven fabric can be stretched, but the filaments are permanently elongated and do not have significant recovery of their prestretched dimension. Thus, the nonwoven fabric following stretching has little retractive force (elastic recovery) and is therefore nonelastic.

The spunbond nonwoven fabric may be bonded by plurality of intermittent bonds. In this regard, thermal point bonding is most preferred. Various thermal point bonding techniques are known, with the most preferred utilizing calender rolls with a point bonding pattern. Any pattern known in the art may be used with typical embodiments employing continuous or discontinuous patterns. Surprisingly, the inventors of the present invention have discovered that point bonding with a calender roll having rod-shaped patterned bonds provides improvements in certain mechanical properties of the nonwoven fabric. As discussed in greater detail below, rod-shaped bond patterns having a cylindrical or rectangular shape that extends in the cross-direction of the fabric have shown surprising improvements in mechanical properties over other bonding patterns.

Preferably, the bonds cover between 6 and 40 percent of the area of the web, more preferably 8 to 25 percent, and most preferably, 8 to 20 percent of the layer is covered. By bonding the web in accordance with these percentage ranges, the filaments are allowed to elongate throughout the full extent of stretching while the strength and integrity of the fabric is maintained.

Multicomponent Fibers

A further aspect of the invention is directed to multicomponent fibers in which a first component comprises the polymer blend described above and at least one second polymer component. In one embodiment, the multicomponent fibers of the invention may include at least two polymer components arranged in structured domains. At least one of the polymer components in the multicomponent fabric is formed of the above described polymer blend in which the polypropylene component and the polyethylene component are immiscible with each other. This results in the polymer blend comprising a dominant continuous phase of the metallocene-catalyzed polypropylene, a dispersed phase of the polyethylene component, and the third polymer component that is at least partially miscible with the other two phases. Other polymer domains of the multicomponent fibers of the invention can be formed of any of the types of fiber forming polymers known in the art such as polyolefins, polyamides, polyesters and the like and the co- and terpolymers and blend thereof.

Nonwoven fabrics in accordance with embodiments of the invention which are comprised of these multicomponent fibers have shown elevated elongation properties. Preferred additional components for the multicomponent fibers include polyethylene, and polypropylene as well as co- and terpolymers and blends thereof.

As is generally well known to those skilled in the art, polymer domains or components are arranged in substantially continuously positioned zones across the cross-section of the multicomponent fiber and extend continuously along the length of the multicomponent fiber. More than two components could be present in the multicomponent fiber. A preferred configuration is a sheath/core arrangement wherein a first component, the sheath, substantially surrounds a second component, the core. The resulting sheath/core bicomponent fiber may have a round or non-round cross-section. Other structured fiber configurations as known in the art can be used including side-by-side, segmented pie, islands-in-the-sea and tipped multilobal structures.

Preferred sheath/core bicomponent fibers for use in making fabrics of this invention can have the higher melting component as the core and the lower melting component as the sheath. For example polyethylene could be used as the sheath and the core could be a higher melting polymer component formed of the polymeric blend. Examples 45 and 46 below were made with this sheath/core structure. Such a structure with polyethylene on the surface allows use of a reduced calender oil bonding temperature thus conserving energy during manufacture of the nonwoven web. The polyethylene surface also provides a cool silky like hand, which is highly desirable in certain Eastern cultures.

A further surprisingly preferred fabric of this invention can be made using sheath/core bicomponent fibers where the higher melting component can be used as the sheath and the lower melting component can be used as the core. Such fabrics, often called reverse bicomponent fabrics, have the sheath formed of the polymer blend a dominant continuous phase of the metallocene-catalyzed polypropylene component, the dispersed phase of polyethylene component, and a third polymer component that is at least partially miscible with the other two phases. In the reverse bicomponent fiber, the core is formed of a lower melting polymer. A particularly preferred lower melting core polymer is polyethylene. Examples 22, 23, 29, 30, 41, and 42 below were made with this Reverse Bicomponent sheath/core structure. Reverse bicomponent fabrics of this invention have the surprising and unexpected properties of showing high extensibility but also having the desirable increased abrasion resistance of a high polypropylene content surface. A high polypropylene surface also provides a warm cottony feel, which can be highly desired in certain Western cultures. A high polypropylene content surface may also provide improved compatibility with certain diaper construction methods, such as hot melt and sonic attachment methods.

Accordingly, it can be seen that nonwoven fabrics in accordance with the present invention may be produced which have high extensibility, tailored surface properties, and can be made using either typical bicomponent or reverse bicomponent structures.

Abrasion Resistance

In addition to improvement in elongation, extensible nonwoven fabrics in accordance with the invention have also exhibited significant improvements in abrasion resistance. An important consideration for selecting a fabric for use in high speed deformation processes is resistance to abrasion. Abrasion resistance is often measured by the Sutherland Ink Rub test where the surface of the fabric is rubbed in a very controlled manner and then loosened fibers are removed and weighed. Results for fabrics of the present invention are shown in Table 7 as Fuzz bonding MD and Fuzz smooth MD with units of mg/cm$^2$. The Sutherland Ink Rub test method as well as results for PE/PP sheath/core high extensible bicomponent fabric not of this invention is disclosed in detail by Lu et al. in WO 2011/088106. A low value suggests that a high resistance to abrasion can be expected.

Results in Table 7, below, show very low Fuzz numbers in the range of 0.02-0.06 for monocomponent Examples of this invention bonded by both the 18% Oval Bonding Pattern as well as by the Cross Direction Rod Bonding Pattern.

Further, for Reverse Bicomponent fabrics in accordance with the present invention, Example 23 (Fuzz results at 0.02 and 0.06 mg/cm$^2$) and for Example 30 (Fuzz results at 0.05 and 0.05) shown a major advantage of the Reverse Bicomponent fabrics of the present invention. Very high % elongation at very low force values are observed resulting from the combination of the polymer blend in sheath and polyethylene as the core. However at the same time a very high resistance to abrasion is preserved.

Accordingly, extensible nonwoven fabrics in accordance with embodiments of the present invention may exhibit an abrasion resistance from about 0.02 to 0.06 mg/cm$^2$, and in particular, from 0.02 to 0.05 mg/cm$^2$, and more particularly, from about 0.02 to 0.04 mg/cm$^2$, and even more particularly, from about 0.02 to 0.03 mg/cm$^2$, as measured by The Sutherland Ink Rub test method.

Fiber Bonding

In a further aspect, embodiments of the present invention are directed fibers comprising the polymer blend of the metallocene-catalyzed polypropylene component, the polyethylene component, and third polymer component in which the fibers have been calendered bonded with rod shaped bond patterns that extend in the cross direction (CD) of the web. In particular, the inventors of the present invention have discovered that CD bonding with rod shaped bonds have significant improvements in both machine direction (MD) and CD elongation in comparison to oval shaped bond patterns. These improvements are demonstrated in the Tables below which is based on results from the examples, which are provided below. In each Table, similar fabrics were produced under similar conditions with the exception of bond pattern. The data from Tables 1-4 is derived from the data in Table 8 below.

TABLE 1

Example 5 vs. Example 14 (monocomponent fibers of polymer blend).

| Comparison of Example 5 (oval bond pattern) vs. Example 14 (CD rod bond pattern) | Percent change |
|---|---|
| Change in MD tensile strength | 2% Decrease |
| Change in CD tensile strength | 6.2% Decrease |
| Change in MD elongation at peak | 0.3% Increase |
| Change in CD elongation at peak | 0.9% Decrease |
| Change in MD elongation at 5N | 46% Increase |
| Change in CD elongation at 5N | 68% Increase |
| Change in MD elongation at 10N | 48% Increase |
| Change in CD elongation at 10N | 15% Increase |

From Table 1, it can be seen that the oval bond pattern vs. CD rod pattern resulted in a minimal and insignificant changes in MD/CD tensile strengths and peak elongations of the web. However, the change in both MD/CD elongations at 5 N and 10 N is very significant and dramatic. In view of the minimal changes in MD/CD tensile strengths and peak elongations, the dramatic increases in elongations at 5 and 10N are highly unexpected. The results indicate that a "flattening" of the stress-strain curve is occurring.

During the ring rolling process, extensible fabrics are generally not stretched to failure during processing. Rather, such extensible fabrics will generally elongate when subjected to forces well below the recorded peak MD or CD tensile and % elongations, such as provided in Tables 1-4. Thus, observed % elongation when exposed to 5 N or 10 N forces may provide a more practical and useful indication of performance during high speed deformation, such as in ring rolling. Thus, for example, in Table 1 little difference is observed between elongation at failure for the oval bonded Example 5 versus the CD rod bonded Example 14. However, the large difference seen at 5 N suggests that Example 14 will be easier to be subjected to high speed deformation with reduced fabric damage than expected for Example 14. The reduction in difference seen for CD at 10 N most likely reflects the fact that 10 N is very near the peak CD tensile for both Examples (see Table 8).

TABLE 2

Example 7 vs. Example 16 (monocomponent fibers of polymer blend).

| Comparison of Example 7 (oval bond pattern) vs. Example 16 (CD rod bond pattern) | Percent change |
|---|---|
| Change in MD tensile strength | 0.3% Increase |
| Change in CD tensile strength | 17.7% Decrease |
| Change in MD elongation at peak | 7.5% Decrease |
| Change in CD elongation at peak | 9.6% Decrease |
| Change in MD elongation at 5N | 22% Increase |
| Change in CD elongation at 5N | 77% Increase |
| Change in MD elongation at 10N | 38% Increase |
| Change in CD elongation at 10N | 68% Increase |

TABLE 3

Example 23 vs. Example 30 (Reverse Bicomponent having a polyethylene sheath and a core of the polymer blend core).

| Comparison of Example 23 (oval bond pattern) vs. Example 30 (CD rod bond pattern) | Percent change |
|---|---|
| Change in MD tensile strength | 19% Decrease |
| Change in CD tensile strength | 28% Decrease |
| Change in MD elongation at peak | 20% Increase |
| Change in CD elongation at peak | 44% Increase |
| Change in MD elongation at 5N | 220% Increase |
| Change in CD elongation at 5N | 276% Increase |
| Change in MD elongation at 10N | 125% Increase |
| Change in CD elongation at 10N | Not measured |

TABLE 4

Example 26 vs. Example 40 (Reverse Bicomponent having polymer blend sheath and polypropylene Zeigler Natta polypropylene core).

| Comparison of Example 26 (oval bond pattern) vs. Example 40 (Honeycomb bond pattern) | Percent change |
|---|---|
| Change in MD tensile strength | 19% Decrease |
| Change in CD tensile strength | 27% Decrease |
| Change in MD elongation at peak | 7% Decrease |
| Change in CD elongation at peak | 1.5% Decrease |
| Change in MD elongation at 5N | 29% Increase |
| Change in CD elongation at 5N | 153% Increase |
| Change in MD elongation at 10N | 78% Increase |
| Change in CD elongation at 10N | 142% Increase |

From Table 4, above, it can be seen honeycomb bond patterns provide improvements in elongation in comparison to oval shaped bond patterns, but not as dramatic as the improvements observed with CD rod shaped bond patterns.

As noted above, nonwoven webs comprised of fibers of the polymeric blend that are bonded with CD rod bond patterns exhibited significant improvement in both MD/CD elongations at 5 N and 10 N in comparison to a similar fabric bonded with oval shaped bond patterns. This result is surprising and unexpected. In particular, nonwoven webs having the inventive polymer blend and being bonded with CD rod bond patterns may exhibit the following range increases in MD and CD elongation at 5 N and 10 N in comparison to webs having oval shaped bond patterns.

| | | | | |
|---|---|---|---|---|
| Increase in MD elongation at 5N | about 20-250% | about 20-225% | about 25-200% | about 25-150% |
| Increase in CD elongation at 5N | about 40-300% | about 50-250% | about 60-175% | about 75-100% |
| Increase in MD elongation at 10N | about 30-225% | about 35-200% | about 45-150% | about 75-125% |
| Increase in CD elongation at 10N | about 15-150% | about 15-125% | about 20-100% | about 25-70% |

The CD rod pattern bonds generally have a length that is about 1.5 to 10× the width. In particular, the CD rod pattern bonds may have an aspect ratio as defined by the length divided by the width that is from about 2 to 10, and in particular, from about 4 to 8.

Generally, it may be desirable for the CD bond patterns to be present in an amount ranging from about 8 to 12% based on the surface area of the nonwoven web, and in particular from about 9 to 11%. In one embodiment, the CD bond patterns cover about 10% of the nonwoven web surface.

High Speed Deformation

Extensible nonwoven webs in accordance with embodiments of the present invention may be particularly useful in applications where high speed deformation is desirable. In particular, nonwoven webs in accordance with the present invention may be incrementally stretched by mechanically applying a tensile force against the composite sheet material in one or more directions. The stretching improves the overall drape and feel of the composite sheet material. In one embodiment, the composite sheet material may be stretched by passing the composite sheet material through one or more incremental stretching rollers. The activation process generally incrementally stretches the composite sheet material about 1.1 to 10.0 fold. In advantageous embodiments, the composite sheet material is stretched or drawn to about 2.5 times its initial length. Incremental stretching in accordance with the present invention may be accomplished by any means known in the art.

A number of different stretchers and techniques may be employed to stretch the composite sheet material. Incremental stretching can be accomplished using, for example, a diagonal intermeshing stretcher, cross direction ("CD") intermeshing stretching equipment, machine direction ("MD") intermeshing stretching equipment.

An exemplary configuration of one suitable incremental stretching system is shown in FIG. 1. The incremental stretching system 200 generally includes a pair of first 202 (e.g., top) and second 204 (e.g., bottom) stretching rollers positioned so as to form a nip. The first incremental stretching roller 202 generally includes a plurality of protrusions 206, such as raised rings, and corresponding grooves 208, both of which extend about the entire circumference of the first incremental stretching roller 202. The second incremental stretching roller 204 similarly includes a plurality of protrusions 206, such as raised rings, and corresponding grooves 208 which also both extend about the entire circumference of the second incremental stretching roller 204. The protrusions 206 on the first incremental stretching roller 202 intermesh with or engage the grooves 208 on the second incremental stretching roller 204, while the protrusions on the second incremental stretching roller 204 intermesh with or engage the grooves on the first incremental stretching roller 202. As the extensible nonwoven fabric 10 passes through the incremental stretching system 200 it is subjected to incremental drawing or stretching in the cross machine ("CD") direction. In advantageous embodiments the protrusions are formed by rings, and the incremental stretching system is referred to as "ring-rolling."

Figure 3:
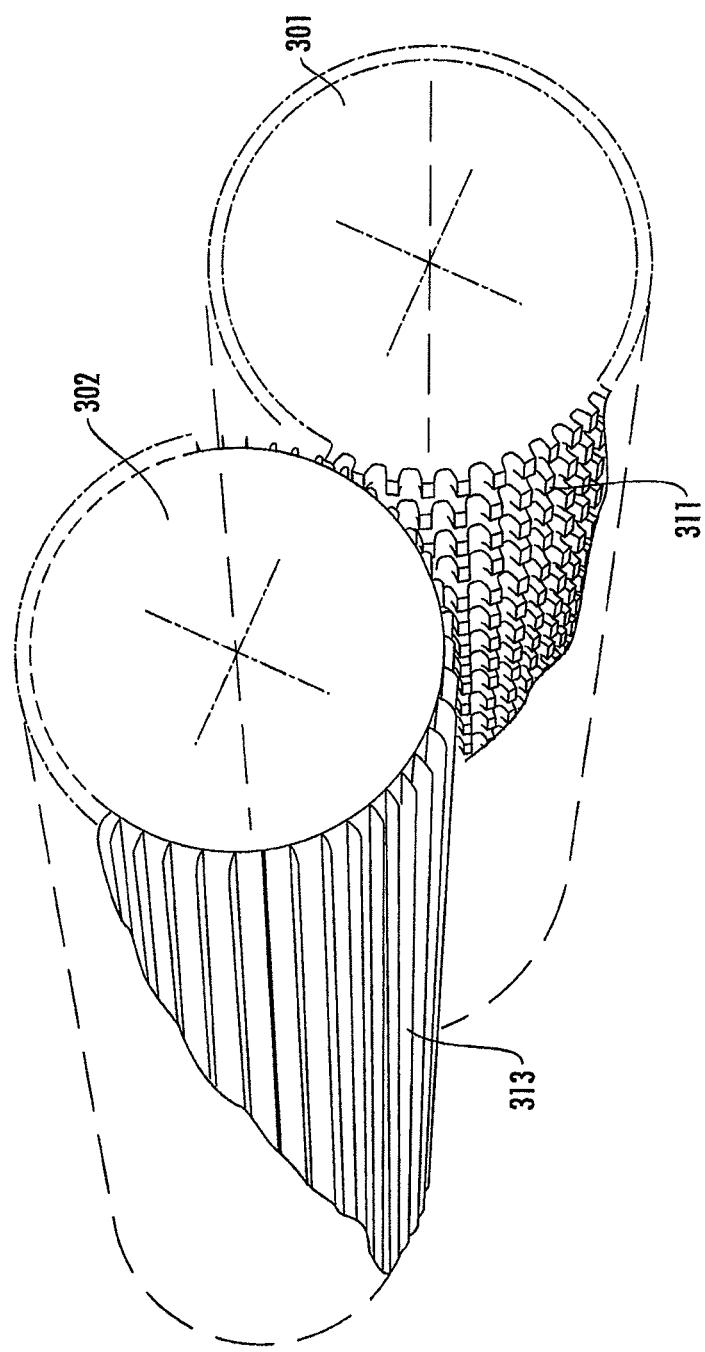
FIG. 3 illustrates an incremental stretching system in accordance with another aspect of the present invention.

Alternatively or additionally, the composite sheet material may be incrementally drawn or stretched in the machine direction ("MD") using one or more incremental stretching systems, such as provided in FIG. 1. As shown in FIG. 3, MD incremental stretching systems 220 similarly include a pair of incremental stretching rollers 222, 224 with intermeshing protrusions 226 and grooves 228. However, the protrusions and grooves within MD incremental stretching systems generally extend parallel to the axis of the roller across the width of the roller, rather than around its circumference. As the extensible nonwoven fabric 10 passes through the incremental stretching system 220 it is subjected to incremental drawing or stretching in the machine ("MD") direction. Methods of incrementally stretching a sheet material are discussed in greater detail in U.S. Pat. No. 6,994,763.

Another type of stretching apparatus useful in the present invention is described in commonly owned U.S. Pat. No. 6,344,102. This apparatus includes a roll assembly comprising a cooperating pair of cylindrical rolls, as shown in FIG.

Figure 4:
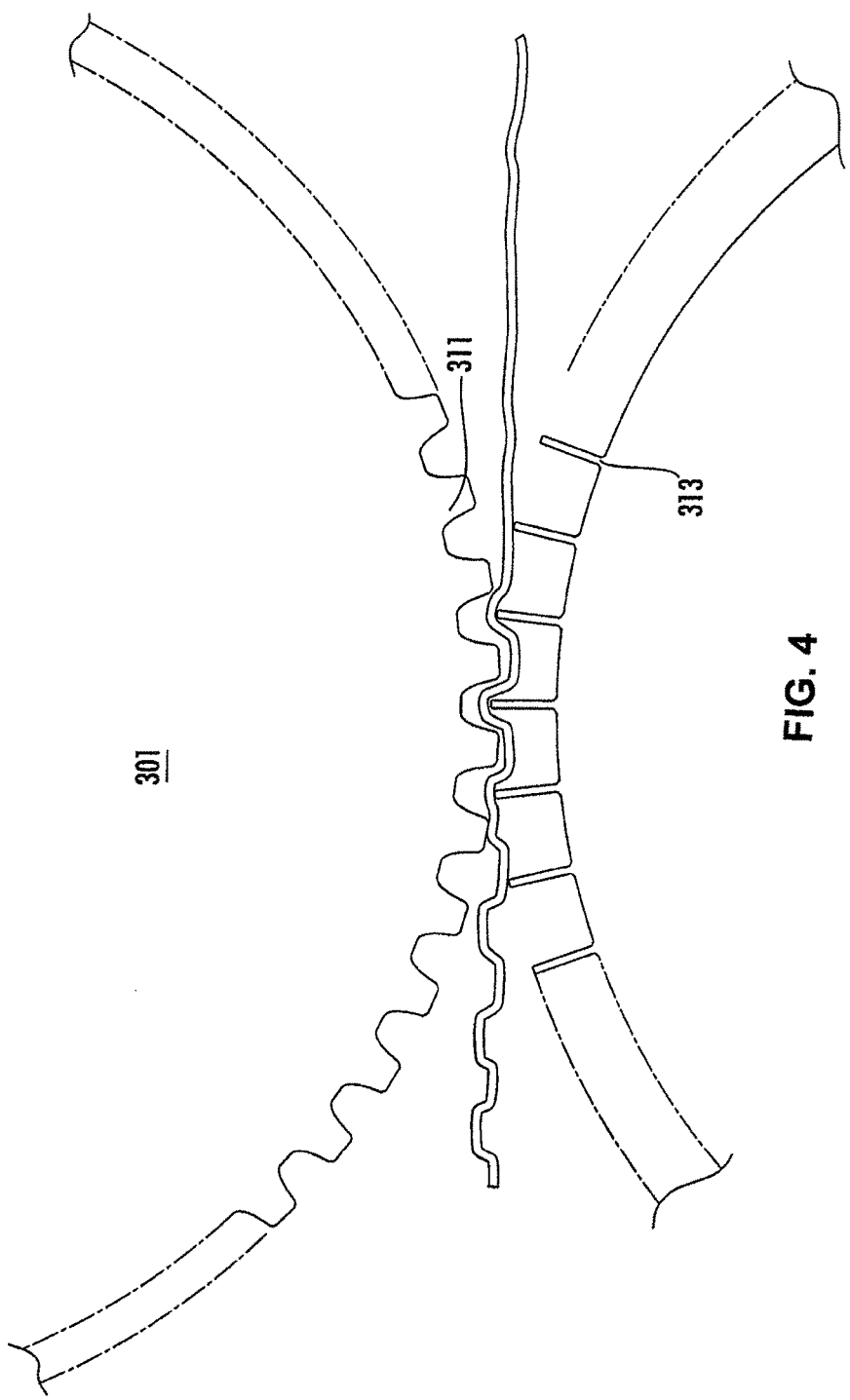
FIG. 4 is a fragmentary cross-sectional view of the roll pair of FIG. 3.

3. A first roll 301 includes a plurality of projections 311 that extend radially outwardly from the surface of the roll. The other roll 302 includes blades 313 extending radially outwardly from the surface of the roll and longitudinally across the width of the roll parallel to the rotational axis of the roll. The blades 313 intermesh with the projections 311 on the first roll, as shown in FIG. 4. As the composite sheet material passes between the rolls 301, 302, the material is driven by the blades into the recesses around the projections on the first roll 301. The extensible polymer fibers in the composite sheet material are incrementally elongated by deep embossing as they form around the projections, both softening and bulking the sheet material.

Figure 5:
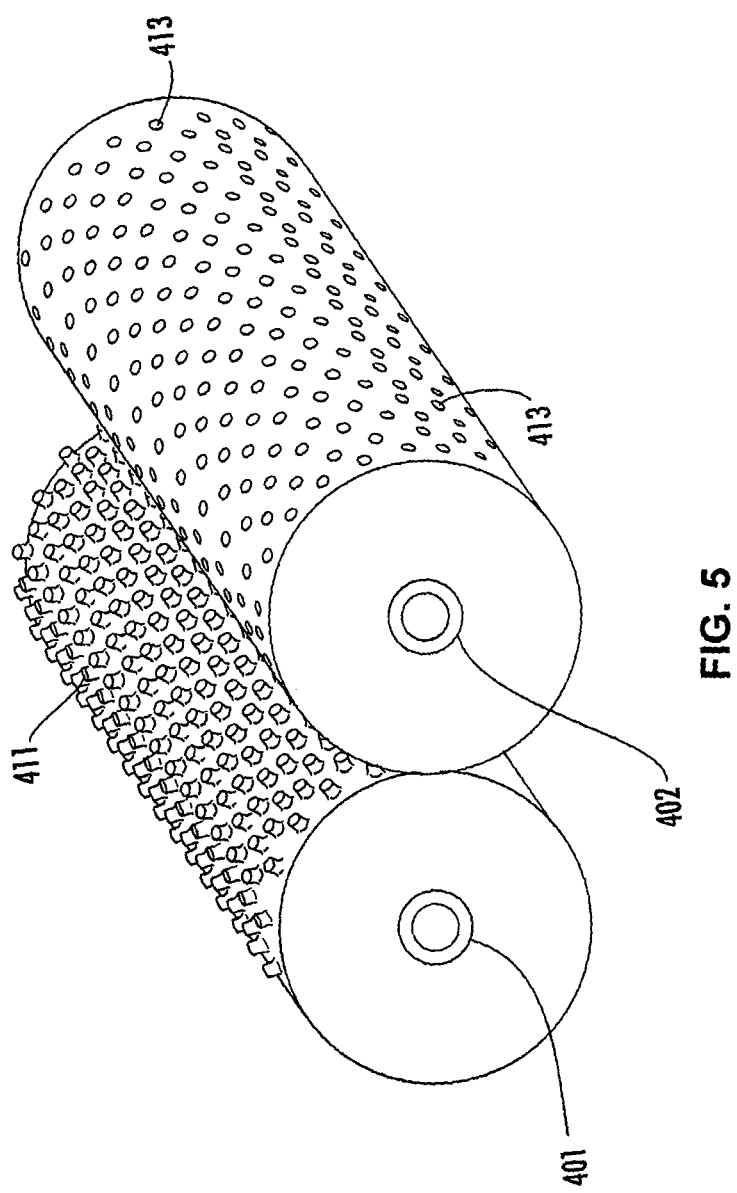
FIG. 5 illustrates an incremental stretching system in accordance with yet another aspect of the present invention.
Figure 6:
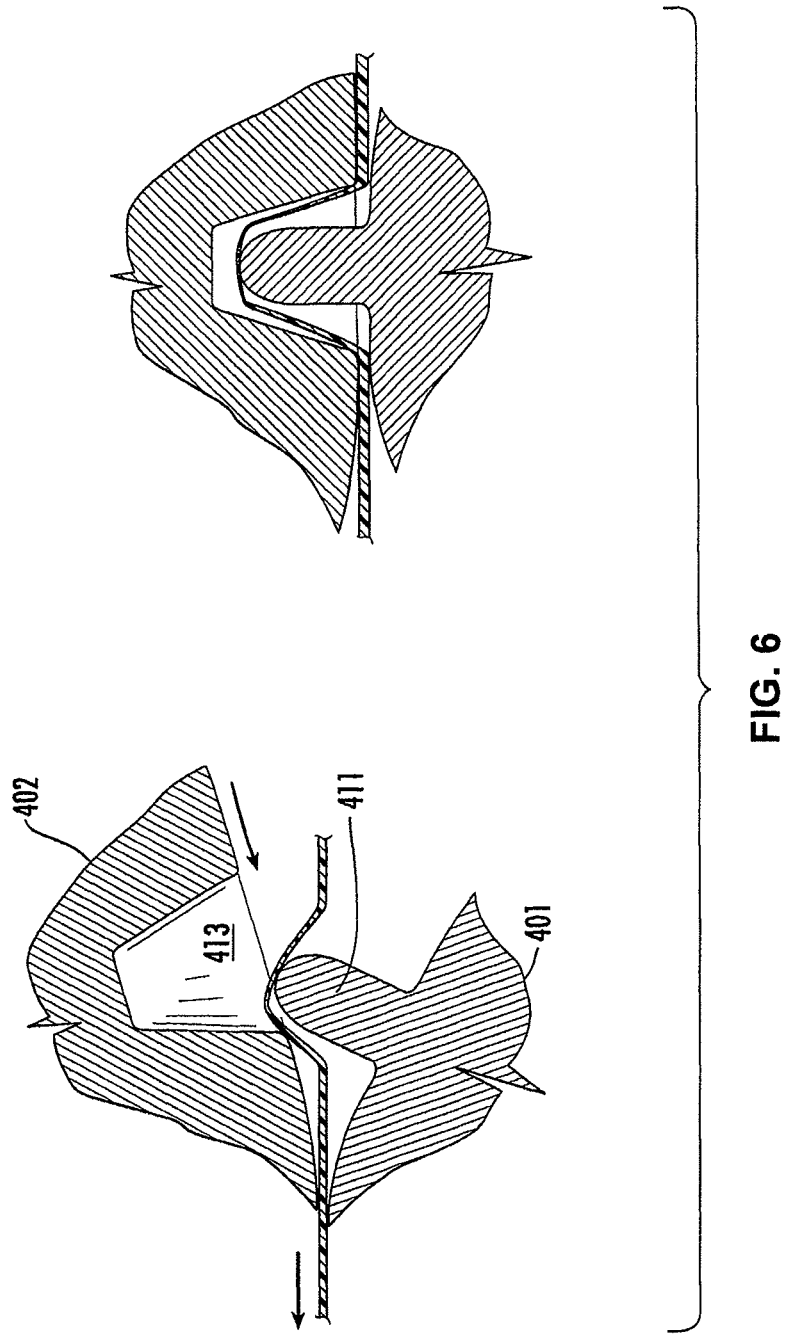
FIG. 6 is a fragmentary cross-sectional view of the roll pair of FIG. 5.

Another type of stretching apparatus useful in the present invention is described in commonly owned U.S. Application 60/763,543 and is shown in FIG. 5 and includes a roll assembly comprising a pair of cylindrical rolls, 401, 402. A first roll 401 includes a plurality of projections 411 that extend radially outwardly from the surface of the roll and can have a generally cylindrical or tapered truncated frustoconical shape. The other roll 402 includes radially oriented recesses 413 correspondingly positioned opposite the projections 411 and correspondingly shaped so as to receive the projections as the rolls are rotated in opposite directions. As the composite sheet material passes between the rolls 401, 402, the material is driven by the projections 411 into the recesses. As shown in FIG. 6, the projections each include an outermost surface portion that is positioned for contacting a discrete portion of the sheet material and for entering a corresponding recess on the opposite roll. As a result, the sheet material is incrementally stretched by deep embossing in discrete areas or zones surrounding the point of contact by the projection as the projection and the sheet material enter into a corresponding recess.

Figure 7:
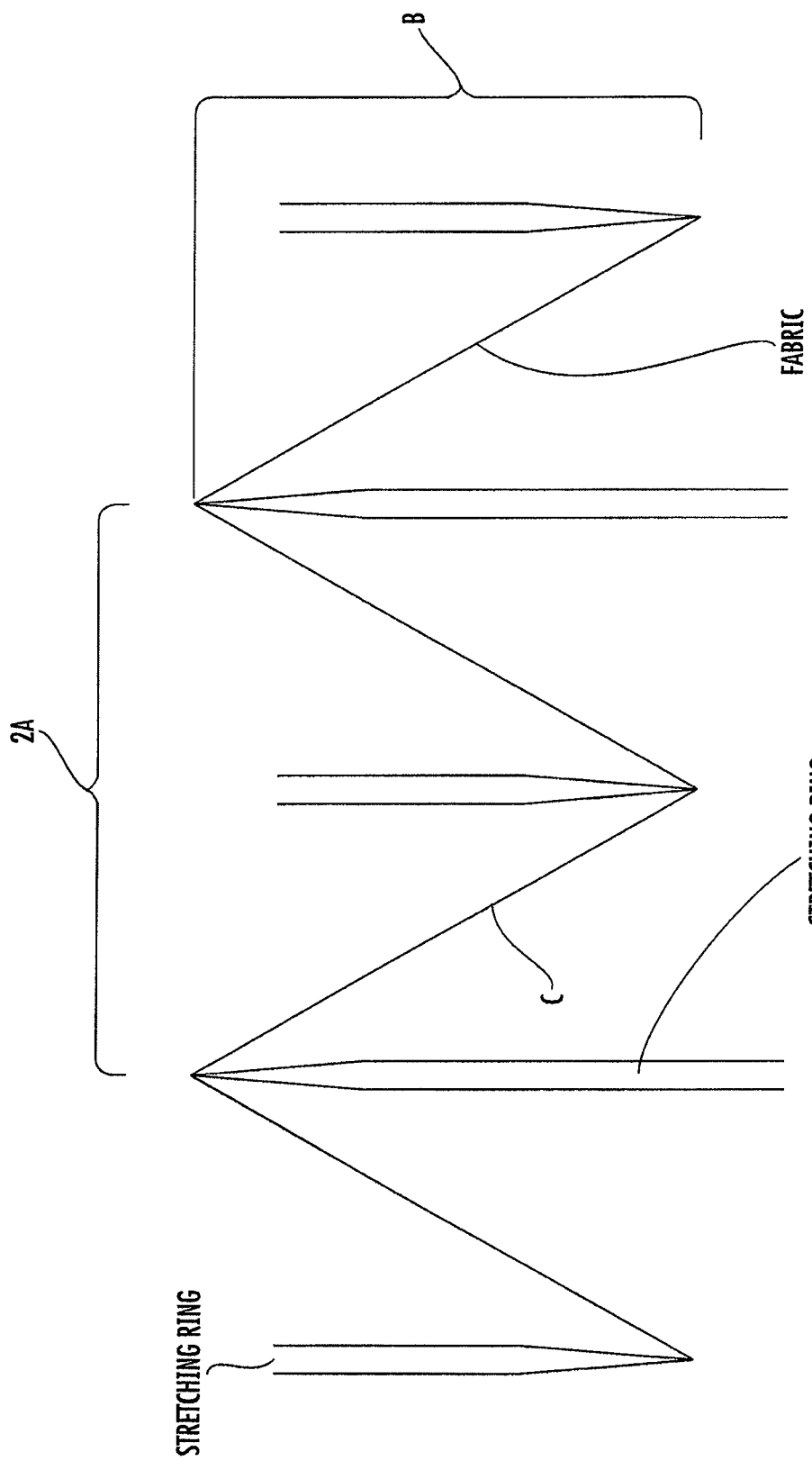
FIG. 7 is a schematic diagram showing how the percent elongation of a material can be measured using ring-rolling.

As noted above, stretching of the composite sheet material subjects portions of the sheet to tensile stress in one or more directions. In the absence of fibers and filaments that are extensible, the application of stress may cause the composite to rupture or tear. As a result, the composite sheet material may be unacceptable for its intended purpose. In preferred embodiments of the present invention, the extensible nonwoven fabric can be stretched at least 150% without rupture, and preferably at least 200% without rupture. A suitable procedure for testing whether a sample can be stretched to this extent involves incrementally stretching the sample in the cross direction by ring-rolling using rolls with circumferentially extending rings. By adjusting the depth of engagement of the rings, the percent elongation can be controlled. As shown in FIG. 7, given the spacing 2A between adjacent rings and the depth of engagement of the rings B, the percent elongation of the material can best be approximated by the formula:

% Elongation=$(\sqrt{(A^2+B^2)}-A)/A \times 100$

As noted previously, embodiments of the present invention are directed to extensible polymeric fibers that can be used to prepare nonwoven fabrics having improved elongation, drape, and abrasion resistance.

A nonwoven fabric may be subjected to a pre-activation test to determine whether the nonwoven fabric has sufficient elongation and tensile strength to be suitable for incremental stretching. In particular, U.S. Pat. No. 8,226,626 describes a pre-activation test having a first tensile test that is intended to mimic the behavior of a nonwoven web during mechanical activation in the CD direction of a nonwoven web. This test is done following EDANA method 20.2-89 with the following changes. A specimen measuring 10 mm (along the CD of the web) by 25 mm (along the MD of the web) of a given nonwoven web is delicately cut from the web. The tensile curve of this specimen is obtained by gripping the edges parallel to the Machine Direction of the specimen with clamps connected to a tensile tester such as a tester from MTS. The gauge length (i.e. clamp to clamp separation) is approximately 5 mm. The tensile curve is obtained at a cross-head displacement speed of approximately 2 mm/s. In order to minimize the influence of the basis weight of each web sample being tested, each curve is normalized for the basis weight of the sample being tested (i.e. the values of the force applied are divided by the value of the aggregate basis weight of the web sample being tested). The elongation of each sample is reported on the x axis in percent elongation while the force applied to each sample is reported on the y axis in Newton per centimeter grams ($Nm^2/gcm$). The specimen is pulled until it ruptures (i.e. the post peak force response reaches a value less than 10% of the peak force). Results of various tensile tests are represented in FIGS. 8-10.

Figure 8:
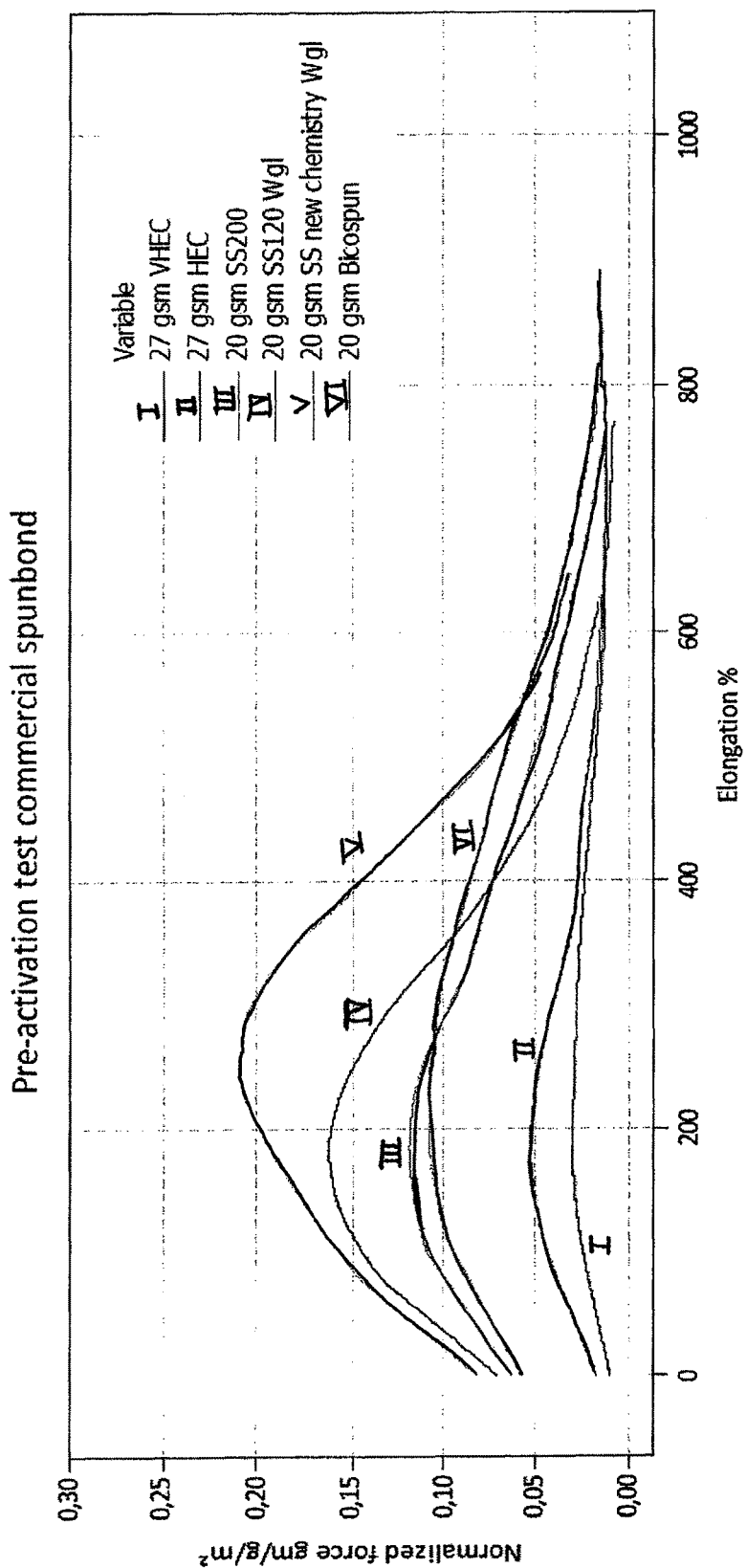
FIGS. 8-12 represent tensile curves for various nonwoven webs.

In FIG. 8, the tensile curve represented by Roman Numerals I and II are obtained from commercially available carded polypropylene nonwovens having a basis weight of 27 g/m². Both of these nonwovens are available from Fitesa, Simpsonville. The tensile curve represented by Roman Numeral III is obtained from nonwoven comprising filaments comprised of a blend of a Zeigler-Natta catalyzed polypropylene, polyethylene, and a polypropylene copolymer having a basis weight of 20 g/m², available from Fiberweb, France (Fiesheim, France) under the product name Sofspan 200. It is believed that this nonwoven product is similar to Comparative Example 1 of Table 5, and is made by a propriety spunbond process generally known in the art as STEX. The nonwoven fabric is approximately 12% point bonded with circular bond patterns. The tensile curve represented by Roman Numeral IV is obtained from a nonwoven comprised of a blend of a Zeigler-Natta catalyzed polypropylene, polyethylene, and a polypropylene copolymer (see Comparative Example 33 in Table 10 below). The tensile curve represented by Roman Numeral V is obtained from a nonwoven comprised of a blend of a metallocene catalyzed polypropylene, polyethylene, and a polypropylene copolymer (see Example 44 in Table 14 below). The tensile curve represented by Roman Numeral VI is obtained from a 70:30 bicomponent filament nonwoven having a polypropylene (PP) core and a polyethylene (PE) sheath having a basis weight of 20 g/m², available from Fitesa, Italy.

Figure 9:
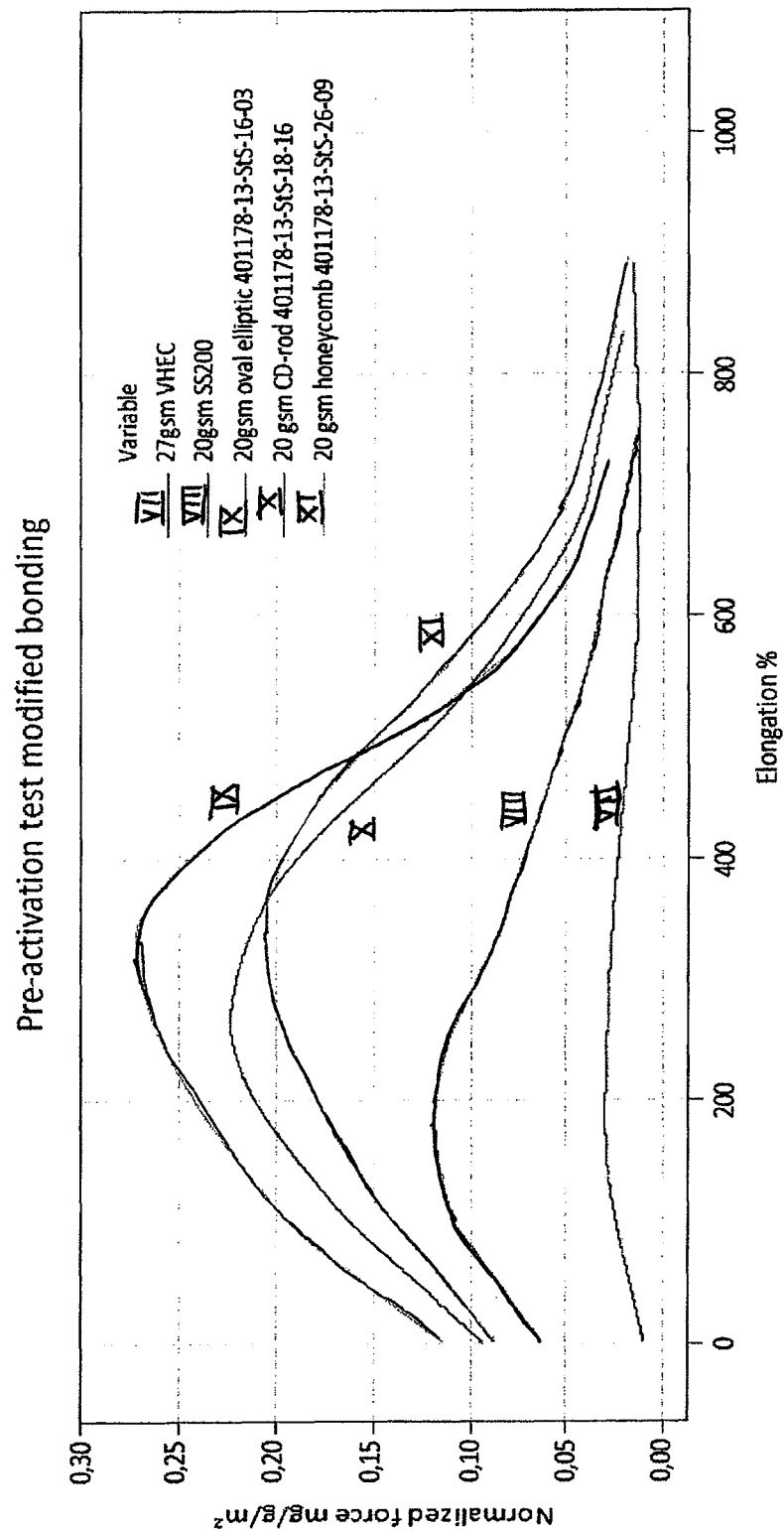

In FIG. 9, pre-activation test was used to evaluate the effects of bonding parameters on % elongation. As shown in FIG. 10, the tensile curve represented by Roman Numerals VII was obtained from a commercially available carded polypropylene nonwoven having a basis weight of 27 g/m² (see description of Roman Numeral I discussed above). The tensile curve represented by Roman Numeral VIII is obtained from the same material for Roman Numeral III described above. The tensile curve represented by Roman Numeral IX is obtained from a nonwoven comprised of a blend of a metallocene catalyzed polypropylene, polyethylene, and the third polymer component (e.g., a polypropylene copolymer) (see Example 6 in Table 5 below). The tensile curve represented by Roman Numeral X is obtained from a nonwoven comprised of a blend of a metallocene catalyzed polypropylene, polyethylene, and a third polymer component (e.g., a polypropylene copolymer) (see Example 15 in Table 5 below), bonded with a cross-direction rod bonding pattern. The tensile curve represented by Roman Numeral XI is obtained from a nonwoven comprised of a blend of a metallocene catalyzed polypropylene, polyethylene, and the third polymer component (e.g., a polypropylene copolymer) (see Example 34 in Table 5 below), bonded with a honeycomb bonding pattern.

Figure 10:
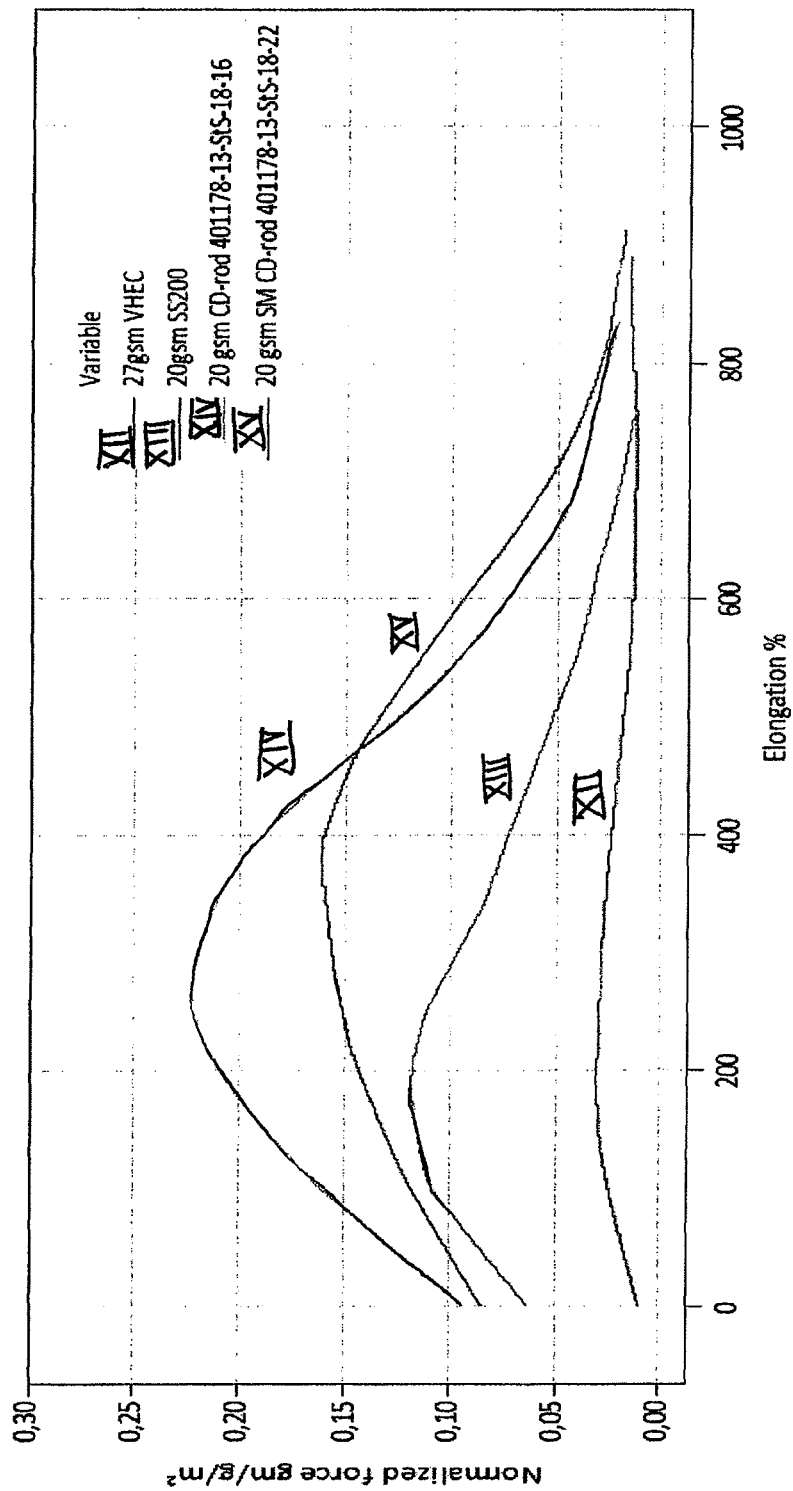

In FIG. 10, the pre-activation test was used to evaluate a simulated spunbond/meltblown/spunbond (SMS) nonwoven fabric. In particular, a composite nonwoven fabric was formed comprising a spunbond layer (18 g/m$^2$) formed of filaments comprising a blend of a metallocene catalyzed polypropylene, polyethylene, and the third polymer component (e.g., a polypropylene copolymer), and second meltblown layer (2 g/m$^2$) formed of a meltblown grade polypropylene, polyethylene, and a polypropylene copolymer was evaluated. Although the resulting nonwoven fabric was not a true SMS, it is expected that an SMS fabric would have properties that at a minimum are similar to the SM nonwoven fabric evaluated in FIG. 10.

The tensile curve represented by Roman Numerals XII was obtained from a commercially available carded polypropylene nonwoven having a basis weight of 27 g/m$^2$, which is the same material for Roman Numeral I discussed above. The tensile curve represented by Roman Numeral XIII is obtained from the same material for Roman Numeral III described above. The tensile curve represented by Roman Numeral XIV is obtained from a nonwoven comprised of a blend of a metallocene catalyzed polypropylene, polyethylene, and the third polymer component (e.g., a polypropylene copolymer) (see Example 15 in Table 5 below). The tensile curve represented by Roman Numeral VX is obtained from a SMS simulated nonwoven comprised of a layer having filaments comprised of a blend of a metallocene catalyzed polypropylene, polyethylene, and a polypropylene copolymer, and a meltblown layer comprised of meltblown fibers comprising a polypropylene, and having a basis weight of 20 g/m$^2$. (See Simulated SMS Example discussed below).

The charts represented in FIGS. 8-10 are based on data that is derived from the Pre-Activation Tensile Test. This test provides a view of how the Force needed to deform a nonwoven changes as the fabrics is elongated. As noted above, the test utilizes a narrow cross-head (5 mm) and the nonwoven is rapidly elongated a rate of 120 mm/minute or 2 mm/sec. In other words, the nonwoven will be elongated to 100% its original distance in approximately more than 2 seconds. The narrow gauge of the cross-head coupled with the rapid rate of elongation mean allows for little opportunity for the fibers in the nonwoven to rearrange due to the elongation. Rather, the fibers themselves must elongate and/or break out of the thermobonds holding the web structure of the nonwoven together.

This test was used to generate the tensile curves in FIGS. 8-10 that shows both the Maximum force needed to extend the fabric is important, but also important is the absolute value of the slope for Force decay as the nonwoven yields after the maximum force is reached. See Table 15, below. Nonwovens that exhibit a reduced damage from high speed deformation, such as happens during ring rolling, show an intermediate maximum force at an extended elongation. The nonwovens then show a rather slow rate of decay in Force as elongation continues.

At the same time, the total energy under the curve is also important since this provides an indication of the toughness of the fabric. See Table 11 below. It is important to note that during elongation, such as in Ring Rolling, the nonwoven may not be stretched to failure. Thus, nonwovens showing a higher area under the stress/strain curve in this test will more likely still be able to provide some resistance to over extension in, for example, an elastic laminate made using the nonwoven that is subsequently ring rolled. The ring rolled laminate made using the inventive nonwovens must extend as stretched, but then resist over extension if the elongation continues. For example, in the case where the laminate is used in the construction of a diaper, the caregiver continues to pull on the diaper ear. This resistance tells the caregiver that the diaper will be tight enough to hold the diaper on the child but will not cause red marks on the child or actually break, wasting the diaper.

A review of the tensile curves in FIG. 9 shows several advantages of the inventive nonwovens. Note that the nonwovens represented by Roman Numerals IX-XI show a low rise to peak Force, and a rather slow decay. In each case, a large area under the curve is observed suggesting a high degree of toughness for the nonwoven. Note further, that each of these nonwovens show high elongation and high toughness (more area under the stress-strain curve), in comparison to the Sofspan 200 nonwoven (identified by Roman Numeral VIII. The tensile curve also demonstrates that the details of the stress strain curve can be varied by combining the improved polymeric blend with different choices in bond pattern design. Accordingly, the inventive blend combined with bonding choices offers the market new opportunities to design improved elastic laminates that can be used in a wide variety of articles, such as in diaper back ears.

Extensible nonwoven fabrics in accordance with embodiments of the present invention may be used in a wide variety of applications. In one embodiment, the extensible nonwoven fabric may be combined with one or more additional layers to form a laminate. In particular, a laminate including any of the nonwoven fabrics previously discussed may be adapted for use in a disposable absorbent article such as a diaper, a pant, an adult incontinence product a sanitary napkin or any other article that may benefit from having at least a portion thereon that is elastically stretchable. In one embodiment, ears or side panels may be cut from such a stretchable laminate and one side edge of the ear may be attached to the chassis of a disposable absorbent article.

In another embodiment, any such laminate may be used as an integral outer cover for an absorbent article. A typical chassis of a disposable absorbent article may include a liquid pervious top sheet, a liquid impervious backsheet and an absorbent core disposed between the topsheet and the backsheet. An absorbent article may also include any features that may be suitable for such an article and are known in the art.

Nonwoven fabrics of the present invention can also be used in combination with other layers to form composite fabrics, such as one or more meltblown layers and/or spunbond bond layers. In one embodiment, nonwoven fabrics in accordance with the present invention can be used to prepare a spunbond/meltblown/spundond (SMS) fabric.

In particular, nonwoven fabrics and laminates incorporating such fabrics may be adapted for use in a disposable absorbent article such as a diaper, a pant, an adult incontinence product a sanitary napkin or any other article that may benefit from having at least a portion thereon that is elastically stretchable. In one embodiment, ears or side panels may be cut from an extensible laminate in accordance with embodiments of the present invention and one side edge of the ear may be attached to the chassis of a disposable absorbent article.

In one embodiment, disposable absorbent articles may be prepared that include a back waist region, a crotch region and a front waist region. A pair of ears may be attached along their respective proximal edge to the left and right sides of the disposable absorbent article respectively. The disposable absorbent article may include a fastener such as a mechanical comprising a plurality of extending hooks or an adhesive may be connected to a portion of the ear or side panel about the distal edge of the ear or side panel. Such a fastener may in combination with the extensible laminate may provide for proper placement and attachment of the absorbent article about the lower torso of a wearer.

In another embodiment, any such extensible laminate may be used as an integral outer cover for an absorbent article. A typical chassis of a disposable absorbent article may include a liquid pervious top sheet, a liquid impervious backsheet and an absorbent core disposed between the topsheet and the backsheet. An absorbent article may also include any features that may be suitable for such an article and are known in the art.

The following examples are provided for illustrating one or more embodiments of the present invention and should not be construed as limiting the invention.

EXAMPLES

Nonwoven fabrics in the following examples were prepared via a Reifenhaeuser CB-100 spunbond spinning beam. Unless otherwise indicated all percentages are weight percentages. The materials used in the examples are identified below.

PP-1: SABIC®, 511A; a Ziegler-Natta polypropylene, with a melt flow rate of 25 g/10 min (ASTM D-1238) and a density of 0.91 g/cc (ASTM D-792).

PP-2: LUMICENE®, MR 2001; a metallocene polypropylene, with a melt flow rate of 25 g/10 min (ISO 1133) and a density of 0.905 g/cc (ISO 1183), provided by Total Petrochemicals.

PP-3: LUMICENE®, M3766; a metallocene isotactic polypropylene, with a melt flow rate of 24 g/10 min (ASTM D-1238) and a density of 0.90 g/cc (ASTM D-1505), provided by Total Petrochemicals.

PP-4: Borflow HL508FB, a meltblown propylene available from Borealis and having a melt flow rate (MFR) of 800 g/10 min tested at 190° C./2.16 kg.

PP-5: LUMICENE®, M3866; a Ziegler-Natta polypropylene provided by Total Petrochemicals.

PE: ASPUN™ 6834; a polyethylene polymer resin having a melt index of 17 g/10 min (ISO 1133) and a density of 0.95 g/cc (ASTM D-792), available from Dow Chemical Company.

PE-1: HD6908.19 is a polyethylene resin supplied by ExxonMobil having a melt index in the range of 7.5 to 9 g/10 min (ISO 1133) and a density of 0.9610 to 0.9680 g/cc (ASTM D-792).

3-PC ($3^{rd}$ Polymer Component): Adflex Z 108 S is a thermoplastic polyolefin manufactured using the Lyondell-Basell's proprietary Catalloy process technology having a melt index of 27 g/10 min (ISO 1133) and a density of 0.89 g/cc (ISO 1133/Method A), available from LyondellBasell Polymers.

Test Methods

Air Permeability was measured in accordance with DIN EN ISO 9237 using a Textest FX 3300 tester.

Basis Weight was determined in accordance with DIN-EN 29 073-1 using an AE 240 balance, a sample width of 21.0 cm and a sample length of 29.7 cm.

Titer was determined in accordance with DIN 53811 using an Axioskop 40 (Zeiss) microscope.

High Speed Deformation Simulation (HSDS) exposes the fabric to forces typically experienced during high speed deformation. Generally, the test is indicative of fabric properties in which the fabric is deformed at high speed. The test was performed using a Zwick Roell, TestXpert, V10.11 (Load Cell 100 N) with a clamp distance of 5 mm, a crosshead speed of 800 mm/min, sample width of 25 mm, and a preload of 0.1 N.

Test 10 is determined using Tensile Test (Mode II) as set forth in U.S. Pat. No. 8,168,853, the contents of which are hereby incorporated by reference in their entirety. In Test 10 a sample width of 50 mm was used at a cross speed of 500 mm/min, and 50 mm gauge length.

Test 2 is determined as in Test 10 with a 127 mm gauge length, a cross speed 127 mm/min, and a sample width of 25.4 mm wide.

Abrasion Resistance is determined by the accumulation of fuzz using The Sutherland Ink Rub test method as set forth in WO 2011/088106, the contents of which are incorporated by reference. Fuzz is measured both on the bonding side of the fabric and the smooth side of the fabric, and is reported in $mg/cm^2$. Table 7, below, reports abrasion resistance based on fuzz on the bonded side of the fabric, and fuzz on the smooth side of the fabric. MD with respect to Table 7, means that the fabric was rubbed in the machine direction of the fabric.

In the Samples described in Tables 5-11, spunbond nonwoven fabrics were obtained using a Reifenhaeuser spunbond beam equipped with a Hills bicomponent die plate. The core and sheath in each sample were of identical composition so that the resulting fibers would be equivalent to a moncomponent die plate. The processing parameters are provided in Table 6 below.

TABLE 5

| Sample Identification No. | Bonding Pattern | Core Main % | Core Side % | Core Side % | Sheath Main % | Sheath Side % | Sheath Side % | Core content % |
|---|---|---|---|---|---|---|---|---|
| Fiber Composition and Construction ||||||||||
| OVAL BONDING PATTERN ||||||||||
| Comparative Example 1 | Oval | 76% PP-1 | 20% 3-PC | 4% PE | 76% PP-1 | 20% 3-PC | 4% PE | 50 |
| Comparative Example 2 | Oval | 76% PP-1 | 20% 3-PC | 4% PE | ¥) a-1 | 20% 3-PC | 4% PE | 50 |
| Comparative Example 3 | Oval | 76% PP-1 | 20% 3-PC | 4% PE | 76% PP-1 | 20% 3-PC | 4% PE | ÿ0 |

TABLE 5-continued

Fiber Composition and Construction

| Sample Identification No. | Bonding Pattern | Core Main % | Core Side % | Core Side % | Sheath Main % | Sheath Side % | Sheath Side % | Core content % |
|---|---|---|---|---|---|---|---|---|
| Comparative Example 4 | Oval | 76% PP-1 | 20% 3-PC | 4% PE | 76% PP-1 | 20% 3-PC | 4% PE | 50 |
| Comparative Example 5 | Oval | 76% PP-1 | 20% 3-PC | 4% PE | 76% PP-1 | 20% 3-PC | 4% PE | 50 |
| Example 1 | Oval | 76% PP-2 | 20% 3-PC | 4% PE | 76% PP-2 | 20% 3-PC | 4% PE | 50 |
| Example 2 | Oval | 76% PP-2 | 20% 3-PC | 4% PE | 76% PP-2 | 20% 3-PC | 4% PE | 50 |
| Example 3 | Oval | 76% PP-2 | 20% 3-PC | 4% PE | 76% PP-2 | 20% 3-PC | 4% PE | 50 |
| Example 4 | Oval | 76% PP-2 | 20% 3-PC | 4% PE | 76% PP-2 | 20% 3-PC | 4% PE | 50 |
| Example 5 | Oval | 76% PP-2 | 20% 3-PC | 4% PE | 76% PP-2 | 20% 3-PC | 4% PE | 50 |
| Example 6 | Oval | 76% PP-2 | 20% 3-PC | 4% PE | 76% PP-2 | 20% 3-PC | 4% PE | 50 |
| Example 7 | Oval | 76% PP-2 | 20% Comp | 4% PE | 76% PP-2 | 20% 3-PC | 4% PE | 50 |
| Example 8 | Oval | 76% PP-2 | 20% 3-PC | 4% PE | 76% PP-2 | 20% 3-PC | 4% PE | 50 |
| Example 9 | Oval | 76% PP-2 | 20% 3-PC | 4% PE | 76% PP-2 | 20% 3-PC | 4% PE | 50 |
| CD ROD BONDING PATTERN | | | | | | | | |
| Comparative Example 6 | CD-rod | 76% PP-1 | 20% 3-PC | 4% PE | 76% PP-1 | 20% 3-PC | 4% PE | 50 |
| Comparative Example 7 | CD-rod | 76% PP-1 | 20% 3-PC | 4% PE | 76% PP-1 | 20% 3-PC | 4% PE | 50 |
| Comparative Example 8 | CD-rod | 76% PP-1 | 20% 3-PC | 4% PE | 76% PP-1 | 20% 3-PC | 4% PE | 50 |
| Comparative Example 9 | CD-rod | 76% PP-1 | 20% 3-PC | 4% PE | 76% PP-1 | 20% 3-PC | 4% PE | 50 |
| Comparative Example 10 | CD-rod | 76% PP-1 | 20% 3-PC | 4% PE | 76% PP-1 | 20% 3-PC | 4% PE | 50 |
| Comparative Example 11 | CD-rod | 76% PP-1 | 20% 3-PC | 4% PE | 76% PP-1 | 20% 3-PC | 4% PE | 50 |
| Comparative Example 12 | CD-rod | 76% PP-1 | 20% 3-PC | 4% PE | 76% PP-1 | 20% 3-PC | 4% PE | 50 |
| Comparative Example 13 | CD-rod | 76% PP-1 | 20% 3-PC | 4% PE | 76% PP-1 | 20% 3-PC | 4% PE | 50 |
| Comparative Example 14 | CD-rod | 76% PP-1 | 20% 3-PC | 4% PE | 76% PP-1 | 20% 3-PC | 4% PE | 50 |
| Comparative Example 15 | CD-rod | 76% PP-1 | 20% 3-PC | 4% PE | 76% PP-1 | 20% 3-PC | 4% PE | 50 |
| Example 10 | CD-rod | 76% PP-2 | 20% 3-PC | 4% PE | 76% PP-2 | 20% 3-PC | 4% PE | 50 |
| Example 11 | CD-rod | 76% PP-2 | 20% 3-PC | 4% PE | 76% PP-2 | 20% 3-PC | 4% PE | 50 |
| Example 12 | CD-rod | 76% PP-2 | 20% 3-PC | 4% PE | 76% PP-2 | 20% 3-PC | 4% PE | 50 |
| Example 13 | CD-rod | 76% PP-2 | 20% 3-PC | 4% PE | 76% PP-2 | 20% 3-PC | 4% PE | 50 |
| Example 14 | CD-rod | 76% PP-2 | 20% 3-PC | 4% PE | 76% PP-2 | 20% 3-PC | 4% PE | 50 |
| Example 15 | CD-rod | 76% PP-2 | 20% 3-PC | 4% PE | 76% PP-2 | 20% 3-PC | 4% PE | 50 |
| Example 16 | CD-rod | 76% PP-2 | 20% 3-PC | 4% PE | 76% PP-2 | 20% 3-PC | 4% PE | 50 |
| Example 17 | CD-rod | 76% PP-2 | 20% 3-PC | 4% PE | 76% PP-2 | 20% 3-PC | 4% PE | 50 |
| Example 18 | CD-rod | 76% PP-2 | 20% 3-PC | 4% PE | 76% PP-2 | 20% 3-PC | 4% PE | 50 |
| Example 19 | CD-rod | 76% PP-2 | 20% 3-PC | 4% PE | 76% PP-2 | 20% 3-PC | 4% PE | 50 |
| Example 20 | CD-rod | 76% PP-2 | 20% 3-PC | 4% PE | 76% PP-2 | 20% 3-PC | 4% PE | 50 |
| Example 21 | CD-rod | 76% PP-2 | 20% 3-PC | 4% PE | 76% PP-2 | 20% 3-PC | 4% PE | 50 |
| REVERSE BICOMPONENT INVENTIVE BLEND IN SHEATH/PE CORE | | | | | | | | |
| Example 22 | CD-rod | 100% PE | 0 | 0 | 76% PP-2 | 20% 3-PC | 4% PE | 70 |
| Example 23 | CD-rod | 100% PE | 0 | 0 | 76% PP-2 | 20% 3-PC | 4% PE | 50 |
| REVERSE BICOMPONENT INVENTIVE BLEND IN SHEATH/ZIEGLER-NATTA PP CORE | | | | | | | | |
| Example 24 | Oval | 100% PP-1 | — | — | 76% PP-2 | 20% 3-PC | 4% PE | 70 |
| Example 25 | Oval | 100% PP-1 | — | — | 76% PP-2 | 20% 3-PC | 4% PE | 70 |
| Example 26 | Oval | 100% PP-1 | — | — | 76% PP-2 | 20% 3-PC | 4% PE | 50 |
| Example 27 | Oval | 100% PP-1 | — | — | 76% PP-2 | 20% 3-PC | 4% PE | 70 |
| REVERSE BICOMPONENT INVENTIVE BLEND IN SHEATH/PE CORE | | | | | | | | |
| Example 28 | Oval | 100% PE | — | — | 76% PP-2 | 20% 3-PC | 4% PE | 70 |
| Example 29 | Oval | 100% PE | — | — | 76% PP-2 | 20% 3-PC | 4% PE | 70 |
| Example 30 | Oval | 100% PE | — | — | 76% PP-2 | 20% 3-PC | 4% PE | 50 |
| Example 31 | Oval | 100% PE | — | — | 76% PP-2 | 20% 3-PC | 4% PE | 70 |
| HONEYCOMB BONDING PATTERN | | | | | | | | |
| Comparative Example 26 | Honeycomb | 76% 511A | 20% Comp | 4% PE | 76% 511A | 20% 3-PC | 4% PE | 50 |
| Comparative Example 27 | Honeycomb | 76% 511A | 20% Comp | 4% PE | 76% 511A | 20% 3-PC | 4% PE | 50 |
| Comparative Example 28 | Honeycomb | 76% 511A | 20% Comp | 4% PE | 76% 511A | 20% 3-PC | 4% PE | 50 |
| Comparative Example 29 | Honeycomb | 76% 511A | 20% Comp | 4% PE | 76% 511A | 20% 3-PC | 4% PE | 50 |

TABLE 5-continued

| | | Fiber Composition and Construction | | | | | | |
|---|---|---|---|---|---|---|---|---|
| Sample Identification No. | Bonding Pattern | Core Main % | Core Side % | Core Side % | Sheath Main % | Sheath Side % | Sheath Side % | Core content % |
| Comparative Example 30 | Honeycomb | 76% 511A | 20% Comp | 4% PE | 76% 511A | 20% 3-PC | 4% PE | 50 |
| Comparative Example 31 | Honeycomb | 76% 511A | 20% Comp | 4% PE | 76% 511A | 20% 3-PC | 4% PE | 50 |
| Example 32 | Honeycomb | 76% PP-2 | 20% Comp | 4% PE | 76% PP-2 | 20% 3-PC | 4% PE | 50 |
| Example 33 | Honeycomb | 76% PP-2 | 20% Comp | 4% PE | 76% PP-2 | 20% 3-PC | 4% PE | 50 |
| Example 34 | Honeycomb | 76% PP-2 | 20% Comp | 4% PE | 76% PP-2 | 20% 3-PC | 4% PE | 50 |
| Example 35 | Honeycomb | 76% PP-2 | 20% Comp | 4% PE | 76% PP-2 | 20% 3-PC | 4% PE | 50 |
| Example 36 | Honeycomb | 76% PP-2 | 20% Comp | 4% PE | 76% PP-2 | 20% 3-PC | 4% PE | 50 |
| Example 37 | Honeycomb | 76% PP-2 | 20% Comp | 4% PE | 76% PP-2 | 20% 3-PC | 4% PE | 50 |
| Example 38 | Honeycomb | 76% PP-2 | 20% Comp | 4% PE | 76% PP-2 | 20% 3-PC | 4% PE | 70 |
| REVERSE BICOMPONENT INVENTIVE BLEND IN SHEATH/ZIEGLER-NATTA PP CORE | | | | | | | | |
| Example 39 | Honeycomb | 100% PP-1 | — | — | 76% PP-2 | 20% 3-PC | 4% PE | 70 |
| Example 40 | Honeycomb | 100% PP-1 | — | — | 76% PP-2 | 20% 3-PC | 4% PE | 50 |
| REVERSE BICOMPONENT INVENTIVE BLEND IN SHEATH/PE CORE | | | | | | | | |
| Example 41 | Honeycomb | 100% PE | — | — | 76% PP-2 | 20% 3-PC | 4% PE | 70 |
| Example 42 | Honeycomb | 100% PE | — | — | 76% PP-2 | 20% 3-PC | 4% PE | 50 |

TABLE 6

| | | | | | | | | | | | |
|---|---|---|---|---|---|---|---|---|---|---|---|
| | | | SPINNING AND BONDING PARAMETERS | | | | | | | | |
| Sample ID No. | Line settings | Tp kg/h | Quench temp ° C. | Cp mbar | Gap mm | Suction fan % | Basis Weight gsm | Bonding | Bond area % | Embossed temp ° C. | Smooth temp ° C. | Pressure N/mm |
| OVAL BONDING PATTERN | | | | | | | | | | | | |
| Comparative Example 1 | 1 | 180 | 20 | 15 | 18 | 90 | 18 | Oval | 19 | 120 | 120 | 70 |
| Comparative Example 2 | 1 | 180 | 20 | 15 | 18 | 70 | 18 | Oval | 19 | 125 | 125 | 70 |
| Comparative Example 3 | 1 | 180 | 20 | 15 | 18 | 70 | 20 | Oval | 19 | 125 | 125 | 70 |
| Comparative Example 4 | 1 | 180 | 20 | 15 | 18 | 70 | 18 | Oval | 19 | 130 | 130 | 70 |
| Comparative Example 5 | 1 | 180 | 20 | 42 | 18 | 70 | 18 | Oval | 19 | 130 | 130 | 70 |
| Example 1 | 1 | 180 | 20 | 15 | 18 | 70 | 18 | Oval | 19 | 120 | 120 | 70 |
| Example 2 | 1 | 180 | 20 | 15 | 18 | 70 | 18 | Oval | 19 | 125 | 125 | 70 |
| Example 3 | 1 | 180 | 20 | 15 | 18 | 70 | 18 | Oval | 19 | 130 | 130 | 70 |
| Example 4 | 1 | 180 | 20 | 42 | 18 | 70 | 18 | Oval | 19 | 130 | 130 | 70 |
| Example 5 | 1 | 180 | 20 | 15 | 18 | 70 | 20 | Oval | 19 | 125 | 125 | 70 |
| Example 6 | 1 | 180 | 20 | 20 | 18 | 70 | 20 | Oval | 19 | 125 | 125 | 70 |
| Example 7 | 1 | 180 | 20 | 25 | 18 | 70 | 20 | Oval | 19 | 125 | 125 | 70 |
| Example 8 | 1 | 180 | 20 | 30 | 18 | 70 | 20 | Oval | 19 | 125 | 125 | 70 |
| Example 9 | 1 | 112 | 20 | 8 | 24 | 70 | 20 | Oval | 19 | 120 | 120 | 70 |
| CROSS DIRECTION ROD BONDING PATTERN | | | | | | | | | | | | |
| Comparative Example 6 | 1 | 180 | 20 | 15 | 18 | 70 | 18 | CD-rod | 11 | 120 | 120 | 70 |
| Comparative Example 7 | 1 | 112 | 20 | 8 | 18 | 70 | 20 | CD-rod | 11 | 120 | 120 | 70 |
| Comparative Example 8 | 1 | 180 | 20 | 15 | 18 | 70 | 18 | CD-rod | 11 | 125 | 125 | 70 |
| Comparative Example 9 | 1 | 180 | 20 | 15 | 18 | 70 | 20 | CD-rod | 11 | 125 | 125 | 70 |
| Comparative Example 10 | 1 | 180 | 20 | 20 | 18 | 70 | 20 | CD-rod | 11 | 125 | 125 | 70 |
| Comparative Example 11 | 1 | 180 | 20 | 25 | 18 | 70 | 20 | CD-rod | 11 | 125 | 125 | 70 |
| Comparative Example 12 | 1 | 180 | 20 | 30 | 18 | 70 | 20 | CD-rod | 11 | 125 | 125 | 70 |
| Comparative Example 13 | 1 | 180 | 20 | 15 | 18 | 70 | 18 | CD-rod | 11 | 130 | 130 | 70 |
| Comparative Example 14 | 1 | 180 | 20 | 15 | 18 | 70 | 20 | CD-rod | 11 | 130 | 130 | 70 |
| Comparative Example 15 | 1 | 180 | 20 | 42 | 18 | 70 | 18 | CD-rod | 11 | 130 | 130 | 70 |

TABLE 6-continued

SPINNING AND BONDING PARAMETERS

| Sample ID No. | Line settings | Tp kg/h | Quench temp ° C. | Cp mbar | Gap mm | Suction fan % | Basis Weight gsm | Bonding | Bond area % | Embossed temp ° C. | Smooth temp ° C. | Pressure N/mm |
|---|---|---|---|---|---|---|---|---|---|---|---|---|
| Example 10 | 1 | 180 | 20 | 15 | 18 | 70 | 18 | CD-rod | 11 | 120 | 120 | 70 |
| Example 11 | 1 | 180 | 20 | 15 | 18 | 70 | 20 | CD-rod | 11 | 120 | 120 | 70 |
| Example 12 | 1 | 112 | 20 | 8 | 18 | 70 | 20 | CD-rod | 11 | 120 | 120 | 70 |
| Example 13 | 1 | 180 | 20 | 15 | 18 | 70 | 18 | CD-rod | 11 | 125 | 125 | 70 |
| Example 14 | 1 | 180 | 20 | 15 | 18 | 70 | 20 | CD-rod | 11 | 125 | 125 | 70 |
| Example 15 | 1 | 180 | 20 | 20 | 18 | 70 | 20 | CD-rod | 11 | 125 | 125 | 70 |
| Example 16 | 1 | 180 | 20 | 25 | 18 | 70 | 20 | CD-rod | 11 | 125 | 125 | 70 |
| Example 17 | 1 | 180 | 20 | 30 | 18 | 70 | 20 | CD-rod | 11 | 125 | 125 | 70 |
| Example 18 | 1 | 180 | 20 | 15 | 18 | 70 | 18 | rd poly 11 | 11 | 130 | 130 | 70 |
| Example 19 | 1 | 180 | 20 | 15 | 18 | 70 | 20 | CD-rod | 11 | 130 | 130 | 70 |
| Example 20 | 1 | 180 | 20 | 42 | 18 | 70 | 18 | CD-rod | 11 | 130 | 130 | 70 |
| Example 21 | 1 | 180 | 20 | 20 | 18 | 70 | 20 (18 SB + 2 MB) | CD-rod | 11 | 125 | 125 | 70 |
| REVERSE BICOMPONENT INVENTIVE BLEND IN SHEATH/PE CORE | | | | | | | | | | | | |
| Example 22 | 2 | 180 | 20 | 15 | 18 | pol20 | 20 | CD-rod | 11 | 125 | 125 | 70 |
| Example 23 | 2 | 180 | 20 | 15 | 18 | 70 | 20 | CD-rod | 11 | 125 | 125 | 70 |
| REVERSE BICOMPONENT INVENTIVE BLEND IN SHEATH/ZEIGLER-NATTA PP CORE | | | | | | | | | | | | |
| Example 24 | 1 | 180 | 20 | 15 | 18 | 70 | 20 | Oval | 19 | 120 | 120 | 70 |
| Example 25 | 1 | 180 | 20 | 15 | 18 | 70 | 20 | Oval | 19 | 125 | 125 | 70 |
| Example 26 | 1 | 180 | 20 | 15 | 18 | 70 | 20 | Oval | 19 | 125 | 125 | 70 |
| Example 27 | 1 | 180 | 20 | 15 | 18 | 70 | 20 | Oval | 19 | 130 | 130 | 70 |
| REVERSE BICOMPONENT INVENTIVE BLEND IN SHEATH/PE CORE | | | | | | | | | | | | |
| Example 28 | 2 | 180 | 20 | 15 | 18 | 70 | 20 | Oval | 19 | 120 | 120 | 70 |
| Example 29 | 2 | 180 | 20 | 15 | 18 | 70 | 20 | Oval | 19 | 125 | 125 | 70 |
| Example 30 | 2 | 180 | 20 | 15 | 18 | 70 | 20 | Oval | 19 | 125 | 125 | 70 |
| Example 31 | 2 | 180 | 20 | 15 | 18 | 70 | 20 | Oval | 19 | 130 | 130 | 70 |
| Comparative Example 26 | 1 | 180 | 20 | 1 | 18 | 70 | 0 | Honeycomb | 16 | 120 | 120 | 70 |
| Comparative Example 27 | 1 | 80 | 20 | 15 | 18 | 70 | 20 | Honeycomb | 16 | 125 | 125 | 70 |
| Comparative Example 28 | 1 | 180 | 20 | 20 | 18 | 70 | 20 | Honeycomb | 16 | 125 | 125 | 70 |
| Comparative Example 29 | 1 | 180 | 20 | 25 | 18 | 70 | 20 | Honeycomb | 16 | 125 | 125 | 70 |
| Comparative Example 30 | 1 | 180 | 20 | 30 | 18 | 70 | 20 | Honeycomb | 16 | 125 | 125 | 70 |
| Comparative Example 31 | 1 | 180 | 20 | 15 | 18 | 70 | 20 | Honeycomb | 16 | 130 | 130 | 70 |
| HONEYCOMB BOND PATTERN | | | | | | | | | | | | |
| Example 32 | 1 | 180 | 20 | 15 | 18 | 70 | 20 | Honeycomb | 16 | 120 | 120 | 70 |
| Example 33 | 1 | 180 | 20 | 15 | 18 | 70 | 20 | Honeycomb | 16 | 125 | 125 | 70 |
| Example 34 | 1 | 180 | 20 | 20 | 18 | 70 | 20 | Honeycomb | 16 | 125 | 125 | 70 |
| Example 35 | 1 | 180 | 20 | 25 | 18 | 70 | 20 | Honeycomb | 16 | 125 | 125 | 70 |
| Example 36 | 1 | 180 | 20 | 30 | 18 | 70 | 20 | Honeycomb | 16 | 125 | 125 | 70 |
| Example 37 | 1 | 180 | 20 | 15 | 18 | 70 | 20 | Honeycomb | 16 | 130 | 130 | 70 |
| Example 38 | 1 | 180 | 20 | 15 | 18 | 70 | 18 + 2 | Honeycomb | 16 | 125 | 125 | 70 |
| REVERSE BICOMPONENT INVENTIVE BLEND IN SHEATH/ZEIGLER-NATTA PP CORE | | | | | | | | | | | | |
| Example 39 | 1 | 180 | 20 | 15 | 18 | 70 | 20 | Honeycomb | 16 | 125 | 125 | 70 |
| Example 40 | 1 | 180 | 20 | 15 | 18 | 70 | 20 | Honeycomb | 16 | 125 | 125 | 70 |
| REVERSE BICOMPONENT INVENTIVE BLEND IN SHEATH/PE CORE | | | | | | | | | | | | |
| Example 41 | 2 | 180 | 20 | 15 | 18 | 70 | 20 | Honeycomb | 16 | 125 | 125 | 70 |
| Example 42 | 2 | 180 | 20 | 15 | 18 | 70 | 20 | Honeycomb | 16 | 125 | 125 | 70 |

TABLE 7

Fiber and Fabric Properties

| Sample Identification No. | Bw gm | Fiber dtex | Fiber den | Air perm m/min | Fuzz bonding MD mg/cm² | Fuzz smooth MD mg/cm² |
|---|---|---|---|---|---|---|
| OVAL BONDING PATTERN | | | | | | |
| Comparative Example 1 | 17.4 | 2.6 | 2.4 | | | |

TABLE 7-continued

Fiber and Fabric Properties

| Sample Identification No. | Bw gm | Fiber dtex | Fiber den | Air perm m/min | Fuzz bonding MD mg/cm$^2$ | Fuzz smooth MD mg/cm$^2$ |
|---|---|---|---|---|---|---|
| Comparative Example 2 | 17.4 | 2.8 | 2.5 | 281 | 0.02 | |
| Comparative Example 3 | 19.2 | 2.7 | 2.5 | 248 | 0.03 | |
| Comparative Example 4 | 17.3 | 2.9 | 2.6 | | 0.02 | |
| Comparative Example 5 | 17.9 | 2.3 | 2.1 | | | |
| Example 1 | 17.5 | 3.0 | 2.7 | | | |
| Example 2 | 17.5 | 3.2 | 2.9 | 282 | 0.02 | |
| Example 3 | 17.4 | 2.6 | 2.3 | | | |
| Example 4 | 17.7 | 1.9 | 1.7 | | | |
| Example 5 | 19.5 | 2.8 | 2.5 | 245 | 0.03 | |
| Example 6 | 19.6 | 2.6 | 2.4 | 219 | | |
| Example 7 | 19.6 | 2.4 | 2.2 | 203 | 0.06 | |
| Example 8 | 19.6 | 2.2 | 2.0 | 186 | 0.04 | |
| Example 9 | 19.8 | 2.2 | 2.0 | 204 | 0.05 | |
| CROSS DIRECTION ROD BONDING PATTERN | | | | | | |
| Comparative Example 6 | 18.0 | | | | | |
| Comparative Example 7 | 19.6 | 3.0 | 2.7 | 316 | | |
| Comparative Example 8 | 18.2 | | | | | |
| Comparative Example 9 | 20.0 | 3.0 | 2.7 | 310 | 0.05 | 0.03 |
| Comparative Example 10 | 20.3 | 2.9 | 2.6 | 277 | | |
| Comparative Example 11 | 20.4 | 2.5 | 2.2 | 251 | | |
| Comparative Example 12 | 20.5 | 2.5 | 2.3 | 240 | | |
| Comparative Example 13 | 18.1 | | | 340 | | |
| Comparative Example 14 | 19.9 | 3.3 | 3.0 | | | |
| Comparative Example 15 | 18.4 | | | | | |
| Example 10 | 18.5 | | | | | |
| Example 11 | 20.4 | 3.1 | 2.8 | | | |
| Example 12 | 21.1 | 4.1 | 3.7 | 342 | | |
| Example 13 | 18.2 | | | | | |
| Example 14 | 20.1 | 3.3 | 3.0 | 300 | 0.04 | 0.02 |
| Example 15 | 19.7 | 2.8 | 2.5 | 270 | | |
| Example 16 | 20.3 | 2.5 | 2.3 | 242 | | |
| Example 17 | 20.1 | 2.3 | 2.1 | 230 | | |
| Example 18 | 18.1 | | | 309 | | |
| Example 19 | 19.7 | 3.1 | 2.8 | | | |
| Example 20 | 18.5 | | | | | |
| Example 21 | 20.2 | 2.7 | 2.4 | 149 | | |
| REVERSE BICOMPONENT INVENTIVE BLEND IN SHEATH/PE CORE | | | | | | |
| Example 22 | 19.5 | 3.5 | 3.1 | | | |
| Example 23 | 18.8 | 3.4 | 3.1 | 341 | 0.02 | 0.06 |
| REVERSE BICOMPONENT INVENTIVE BLEND IN SHEATH/ZEIGLER-NATTA PP CORE | | | | | | |
| Example 24 | 19.6 | 3.0 | 2.7 | | | |
| Example 25 | 19.5 | 3.2 | 2.9 | | | |
| Example 26 | 19.4 | 3.2 | 2.9 | 250 | 0.06 | 0.06 |
| Example 27 | 19.4 | 3.0 | 2.7 | | | |
| REVERSE BICOMPONENT INVENTIVE BLEND IN SHEATH/PE CORE | | | | | | |
| Example 28 | 19.6 | 3.2 | 2.8 | | | |
| Example 29 | 19.7 | 3.4 | 3.1 | | | |
| Example 30 | 19.7 | 2.8 | 2.5 | 253 | 0.05 | 0.05 |
| Example 31 | 19.7 | 3.0 | 2.7 | | | |
| HONEYCOMB BONDING PATTERN | | | | | | |
| Comparative Example 26 | | | | | | |
| Comparative Example 27 | | | | | | |
| Comparative | | | | | | |

TABLE 7-continued

Fiber and Fabric Properties

| Sample Identification No. | Bw gm | Fiber dtex | Fiber den | Air perm m/min | Fuzz bonding MD mg/cm$^2$ | Fuzz smooth MD mg/cm$^2$ |
|---|---|---|---|---|---|---|
| Example 28 | | | | | | |
| Comparative Example 29 | | | | | | |
| Comparative Example 30 | | | | | | |
| Comparative Example 31 | | | | | | |
| Example 32 | | | | | | |
| Example 33 | | | | | | |
| Example 34 | | | | | | |
| Example 35 | | | | | | |
| Example 36 | | | | | | |
| Example 37 | | | | | | |
| Example 38 | | | | | | |
| Example 39 | | | | | | |
| Example 40 | | | | | | |
| Example 41 | | | | | | |
| Example 42 | | | | | | |

TABLE 8

High Speed Deformation Simulation at 800 mm/min

| Sample ID No. | MDT N/5 cm | CDT N/5 cm | MDE % | CDE % | MDE at 5N % | CDE at 5N % | MDE at 10N % | CDE at 10N % | MD energy at break 1/m$^2$ | CD energy at break 1/m$^2$ | MD Mod at 1% EkPa | CD Mod at 1% EkPa | MD Mod at 5% EkPa | CD Mod at 5% EkPa |
|---|---|---|---|---|---|---|---|---|---|---|---|---|---|---|
| OVAL BONDING PATTERN ||||||||||||||| 
| Comparative Example 1 | 15.4 | 10.6 | 292.7 | 295.9 | 10.9 | 30.0 | 66.8 | 162.9 | 4.8 | 3.7 | 25.92 | 0.49 | 0.58 | 0.35 |
| Comparative Example 2 | 16.0 | 12.5 | 302.2 | 322.8 | 9.9 | 20.1 | 60.7 | 142.8 | 4.7 | 4.2 | 0.93 | 28.22 | 0.61 | 0.40 |
| Comparative Example 3 | 16.1 | 14.1 | 326.2 | 337.3 | 9.5 | 16.1 | 50.9 | 95.2 | 5.0 | 4.9 | 0.89 | 11.62 | 0.60 | 0.45 |
| Comparative Example 4 | 13.4 | 11.4 | 259.6 | 287.9 | 11.7 | 22.9 | 84.3 | 157.3 | 3.6 | 3.6 | 1.27 | 1.15 | 0.53 | 0.38 |
| Comparative Example 5 | 27.4 | 17.2 | 191.8 | 204.0 | 4.0 | 12.0 | 11.3 | 41.5 | 4.5 | 3.3 | 2.06 | 19.01 | 1.15 | 0.58 |
| Example 1 | 14.1 | 11.1 | 342.4 | 342.5 | 9.9 | 23.7 | 97.9 | 187.3 | 4.9 | 4.1 | 34.64 | 23.22 | 0.60 | 0.39 |
| Example 2 | 14.3 | 11.3 | 314.1 | 343.8 | 8.9 | 20.6 | 79.8 | 185.0 | 4.7 | 4.0 | 15.74 | 19.36 | 0.61 | 0.41 |
| Example 3 | 13.3 | 11.6 | 305.8 | 354.4 | 9.6 | 18.8 | 74.4 | 168.3 | 4.4 | 4.2 | 19.46 | 1.57 | 0.59 | 0.42 |
| Example 4 | 23.3 | 15.4 | 267.5 | 277.3 | 4.6 | 13.5 | 14.9 | 65.9 | 5.7 | 4.2 | 1.47 | 0.72 | 0.95 | 0.52 |
| Example 5 | 14.4 | 11.3 | 318.6 | 340.1 | 9.1 | 20.8 | 81.2 | 204.9 | 4.5 | 3.9 | 21.43 | 12.05 | 0.61 | 0.40 |
| Example 6 | 17.9 | 13.6 | 330.6 | 342.6 | 7.3 | 15.8 | 37.6 | 119.9 | 5.8 | 4.8 | 37.22 | 14.64 | 0.72 | 0.45 |
| Example 7 | 19.8 | 15.2 | 318.0 | 333.9 | 6.4 | 15.7 | 26.2 | 81.3 | 5.8 | 4.9 | 1.12 | 14.22 | 0.76 | 0.49 |
| Example 8 | 24.2 | 16.4 | 338.5 | 361.2 | 4.8 | 12.6 | 14.9 | 62.7 | 7.1 | 5.3 | 82.58 | 2.12 | 0.90 | 0.52 |
| Example 9 | 16.3 | 13.5 | 388.4 | 396.6 | 8.3 | 15.7 | 54.7 | 146.2 | 6.1 | 5.4 | 25.93 | 14.82 | 0.63 | 0.45 |
| CD ROD BONDING PATTERN ||||||||||||||| 
| Comparative Example 6 | 12.1 | 9.2 | 368.4 | 376.4 | 25.8 | 60.7 | 188.4 | 269.9 | 4.8 | 4.6 | 1.41 | 0.33 | 0.39 | 0.24 |
| Comparative Example 7 | 12.5 | 10.4 | 419.7 | 464.2 | 19.4 | 45.8 | 213.5 | 320.9 | 5.9 | 6.0 | 0.61 | 25.26 | 0.42 | 0.29 |
| Comparative Example 8 | 13.5 | 9.2 | 365.9 | 382.7 | 17.1 | 54.1 | 143.5 | 248.6 | 5.0 | 4.4 | 19.99 | 12.60 | 0.44 | 0.24 |
| Comparative Example 9 | 13.6 | 10.0 | 340.8 | 389.1 | 16.2 | 47.2 | 136.9 | 290.9 | 5.3 | 4.8 | 17.07 | 0.64 | 0.46 | 0.26 |
| Comparative Example 10 | 17.1 | 11.8 | 324.6 | 341.4 | 12.2 | 34.5 | 64.3 | 137.1 | 6.0 | 5.1 | 1.83 | 1.07 | 0.55 | 0.32 |
| Comparative Example 11 | 18.1 | 13.8 | 308.7 | 308.2 | 10.0 | 24.0 | 44.4 | 114.7 | 5.6 | 5.5 | 0.90 | 25.73 | 0.59 | 0.37 |
| Comparative Example 12 | 21.7 | 14.2 | 291.2 | 266.4 | 7.3 | 20.1 | 23.9 | 85.4 | 6.3 | 5.0 | 1.49 | 1.12 | 0.76 | 0.41 |
| Comparative Example 13 | 12.7 | 9.8 | 329.0 | 384.8 | 18.7 | 54.4 | 151.5 | 207.9 | 4.6 | 4.7 | 0.62 | 22.27 | 0.45 | 0.25 |
| Comparative Example 14 | 14.7 | 10.6 | 357.1 | 385.2 | 14.0 | 48.2 | 109.4 | 201.0 | 5.7 | 5.2 | 14.40 | 0.36 | 0.50 | 0.29 |
| Comparative Example 15 | 21.3 | 12.4 | 180 | 165 | 6.3 | 21.7 | 19.2 | 82.3 | 3.6 | 3.1 | 1.27 | 0.55 | 0.88 | 0.4 |

TABLE 8-continued

High Speed Deformation Simulation at 800 mm/min

| Sample ID No. | MDT N/5 cm | CDT N/5 cm | MDE % | CDE % | MDE at 5N % | CDE at 5N % | MDE at 10N % | CDE at 10N % | MD energy at break 1/m² | CD energy at break 1/m² | MD Mod at 1% EkPa | CD Mod at 1% EkPa | MD Mod at 5% EkPa | CD Mod at 5% EkPa |
|---|---|---|---|---|---|---|---|---|---|---|---|---|---|---|
| Example 10 | | | | | | | | | | | | | | |
| Example 11 | 12.8 | 9.8 | 390.1 | 423.2 | 20.8 | 58.7 | 160.9 | 276.5 | 5.5 | 5.1 | 14.07 | 10.73 | 0.45 | 0.28 |
| Example 12 | 9.6 | 9.1 | 361.7 | 471.7 | 47.5 | 72.5 | 242.6 | 252.6 | 4.3 | 5.6 | 2.28 | 1.59 | 0.38 | 0.31 |
| Example 13 | | | | | | | | | | | | | | |
| Example 14 | 14.1 | 10.6 | 321.7 | 336.8 | 13.3 | 35.0 | 120.4 | 234.7 | 5.0 | 4.8 | 35.93 | 0.46 | 0.51 | 0.33 |
| Example 15 | 16.9 | 11.0 | 291.1 | 296.5 | 10.4 | 42.5 | 65.9 | 165.7 | 5.2 | 4.4 | 21.05 | 0.85 | 0.59 | 0.32 |
| Example 16 | 20.4 | 12.5 | 294.3 | 302.8 | 7.8 | 27.8 | 36.1 | 136.8 | 5.8 | 4.7 | 12.50 | 19.24 | 0.71 | 0.36 |
| Example 17 | 21.8 | 14.6 | 272.1 | 266.6 | 6.5 | 19.3 | 25.1 | 90.6 | 5.7 | 5.0 | 1.04 | 0.55 | 0.76 | 0.42 |
| Example 18 | | | | | | | | | | | | | | |
| Example 19 | 14.7 | 9.8 | 331.9 | 354.4 | 11.7 | 50.7 | 102.9 | 240.8 | 5.4 | 4.4 | 0.79 | 8.29 | 0.55 | 0.29 |
| Example 20 | | | | | | | | | | | | | | |
| Example 21 | 13.6 | 10.5 | 345.1 | 398.0 | 9.6 | 25.4 | 123.5 | 257.0 | 5.0 | 5.2 | 0.89 | 0.60 | 0.60 | 0.41 |
| REVERSE BICOMPONENT INVENTIVE BLEND IN SHEATH/PE CORE | | | | | | | | | | | | | | |
| Example 22 | 9.2 | 6.9 | 415.6 | 448.7 | 51.9 | 125.2 | 311.5 | | 4.2 | 4.1 | 14.93 | 0.73 | 0.34 | 0.21 |
| Example 23 | 9.4 | 6.5 | 424.3 | 527.3 | 48.6 | 192.4 | 344.3 | | 4.7 | 4.2 | 26.35 | 0.33 | 0.34 | 0.16 |
| REVERSE BICOMPONENT INVENTIVE BLEND IN SHEATH/ZIEGLER-NATTA PP CORE | | | | | | | | | | | | | | |
| Example 24 | 19.4 | 15.2 | 294.3 | 296.4 | 6.8 | 12.8 | 27.2 | 63.7 | 5.9 | 5.0 | 23.65 | 34.75 | 0.75 | 0.54 |
| Example 25 | 18.5 | 15.4 | 257.8 | 271.5 | 7.4 | 14.5 | 29.5 | 69.6 | 4.4 | 4.6 | 1.05 | 43.11 | 0.72 | 0.52 |
| Example 26 | 18.7 | 15.3 | 313.3 | 326.0 | 7.6 | 13.1 | 33.6 | 69.8 | 5.8 | 5.2 | 26.45 | 1.08 | 0.71 | 0.52 |
| Example 27 | 19.2 | 15.4 | 268.0 | 269.6 | 7.2 | 13.8 | 29.3 | 64.1 | 5.3 | 4.6 | 32.09 | 54.50 | 0.74 | 0.51 |
| REVERSE BICOMPONENT INVENTIVE BLEND IN SHEATH/PE CORE | | | | | | | | | | | | | | |
| Example 28 | 10.3 | 8.7 | 309.2 | 327.8 | 21.9 | 45.6 | 179.0 | 242.4 | 3.6 | 3.5 | 41.37 | 0.42 | 0.42 | 0.31 |
| Example 29 | 10.5 | 8.5 | 300.0 | 317.9 | 18.4 | 42.7 | 170.2 | 268.6 | 3.5 | 3.1 | 1.85 | 0.42 | 0.44 | 0.30 |
| Example 30 | 11.6 | 9.0 | 353.9 | 365.8 | 15.4 | 50.5 | 153.3 | 288.0 | 4.3 | 3.7 | 21.23 | 1.09 | 0.49 | 0.31 |
| Example 31 | 10.5 | 8.4 | 270.4 | 279.7 | 15.5 | 35.6 | 170.4 | 257.7 | 3.4 | 2.9 | 44.12 | 0.43 | 0.47 | 0.32 |
| HONEYCOMB BONDING PATTERN | | | | | | | | | | | | | | |
| Comparative Example 26 | | | | | | | | | | | | | | |
| Comparative Example 27 | | | | | | | | | | | | | | |
| Comparative Example 28 | | | | | | | | | | | | | | |
| Comparative Example 29 | | | | | | | | | | | | | | |
| Comparative Example 30 | | | | | | | | | | | | | | |
| Comparative Example 31 | | | | | | | | | | | | | | |
| Example 32 | | | | | | | | | | | | | | |
| Example 33 | 13.4 | 10.5 | 333 | 357 | 11.1 | 27.8 | 114.7 | 208 | 4.9 | 4 | 3.94 | 0.53 | 0.56 | 0.37 |
| Example 34 | 15.5 | 11.6 | 339 | 375 | 10.4 | 38.7 | 70.5 | 208.3 | 5.5 | 4.8 | 0.83 | 0.47 | 0.57 | 0.33 |
| Example 35 | 17.3 | 13 | 300 | 328 | 7.2 | 20.3 | 34.4 | 136.4 | 5.8 | 4.3 | 1.1 | 0.67 | 0.73 | 0.44 |
| Example 36 | 20 | 13.9 | 287 | 301 | 6.7 | 17.8 | 26.5 | 111.5 | 6 | 4.3 | 1.21 | 0.62 | 0.76 | 0.45 |
| Example 37 | | | | | | | | | | | | | | |
| Example 38 | | | | | | | | | | | | | | |
| REVERSE BICOMPONENT INVENTIVE BLEND IN SHEATH/ZIEGLER-NATTA PP CORE | | | | | | | | | | | | | | |
| Example 39 | 15.9 | 11.1 | 250 | 279 | 8.4 | 27.9 | 42.2 | 158.1 | 4.9 | 3.8 | 1.57 | 0.95 | 0.68 | 0.33 |
| Example 40 | 15.1 | 11.2 | 290 | 321 | 9.8 | 33.1 | 59.8 | 168.5 | 4.9 | 4.1 | 0.89 | 0.45 | 0.62 | 0.34 |
| REVERSE BICOMPONENT INVENTIVE BLEND IN SHEATH/PE CORE | | | | | | | | | | | | | | |
| Example 41 | 8.9 | 7.8 | 266 | 343 | 25.1 | 78.3 | 273 | 312.8 | 3.3 | 3.1 | 0.6 | 0.36 | 0.4 | 0.26 |
| Example 42 | 9.9 | 7.4 | 326 | 381 | 21.4 | 91.6 | 169.2 | — | 4.0 | 3.3 | 1.98 | 0.36 | 0.42 | 0.24 |

TABLE 9

Tensile test at 200 mm/min

| Sample ID No. | MDT N | CDT N | MDE % | CDE % | MDE at 5N | CDE at 5N | MDE at 10N | CDE at 10N |
|---|---|---|---|---|---|---|---|---|
| OVAL BONDING PATTERN | | | | | | | | |
| Comparative Example 1 | 21.0 | 16.0 | 136 | 136 | 6.5 | 16.4 | 23.5 | 48.4 |
| Comparative Example 2 | 21.5 | 15.6 | 129 | 126 | 5.6 | 16.0 | 19.8 | 47.1 |

TABLE 9-continued

Tensile test at 200 mm/min

| Sample ID No. | MDT N | CDT N | MDE % | CDE % | MDE at 5N | CDE at 5N | MDE at 10N | CDE at 10N |
|---|---|---|---|---|---|---|---|---|
| OVAL BONDING PATTERN |||||||||
| Comparative Example 3 | 25.4 | 17.5 | 141 | 129 | 4.6 | 13.2 | 15.3 | 37.8 |
| Comparative Example 4 | 20.2 | 16.0 | 108 | 126 | 5.3 | 15.4 | 18.7 | 44.8 |
| Comparative Example 5 | 46.0 | 27.4 | 95 | 102 | 2.1 | 8.8 | 5.1 | 20.1 |
| Example 1 | 20.2 | 15.3 | 156 | 149 | 5.1 | 14.5 | 22.0 | 52.5 |
| Example 2 | 20.9 | 14.8 | 156 | 138 | 4.8 | 14.5 | 20.5 | 52.1 |
| Example 3 | 17.9 | 14.5 | 112 | 129 | 4.5 | 13.5 | 18.9 | 48.0 |
| Example 4 | 38.2 | 22.1 | 118 | 120 | 2.1 | 10.0 | 5.6 | 26.7 |
| Example 5 | 23.2 | 16.5 | 146 | 134 | 3.8 | 12.1 | 13.9 | 38.6 |
| Example 6 | 28.1 | 19.9 | 149 | 149 | 3.4 | 10.6 | 11.3 | 31.7 |
| Example 7 | 32.5 | 22.0 | 147 | 144 | 2.8 | 9.7 | 8.5 | 27.5 |
| Example 8 | 37.5 | 23.9 | 146 | 145 | 2.5 | 9.4 | 7.2 | 26.1 |
| Example 9 | 27.5 | 19.0 | 185 | 160 | 3.6 | 10.2 | 12.8 | 33.6 |

TABLE 10

Tensile test at 100 mm/min

| Sample ID No. | MDT N/cm | CDT N/cm | MDE % | CDE % | MDE at 5N % | CDE at 5N % | MDT at 5% N/cm | CDT at 5% N/cm | MDE at 10N % | CDE at 10N % | MDT at 10% N/cm | CDT at 10% N/cm | MDT at 33% N/cm | CDT at 33% N/cm | Break-point % | Break-point % |
|---|---|---|---|---|---|---|---|---|---|---|---|---|---|---|---|---|
| OVAL BONDING PATTERN |||||||||||||||||
| Comparative Example 1 | 4.06 | 3.11 | 142 | 134 | 7.2 | 17.2 | 0.79 | 0.36 | 26.5 | 51.8 | 1.2 | 0.6 | 2.2 | 1.6 | 156 | 153 |
| Comparative Example 2 | 4.29 | 3.18 | 133 | 139 | 5.8 | 16.4 | 0.92 | 0.40 | 21.0 | 49.3 | 1.4 | 0.7 | 2.4 | 1.6 | 148 | 152 |
| Comparative Example 3 | 4.74 | 3.53 | 135 | 142 | 4.8 | 14.0 | 1.02 | 0.46 | 17.0 | 40.5 | 1.5 | 0.8 | 2.7 | 1.8 | 148 | 155 |
| Comparative Example 4 | 4.20 | 3.11 | 127 | 127 | 5.6 | 15.7 | 0.94 | 0.42 | 20.1 | 46.6 | 1.4 | 0.7 | 2.5 | 1.7 | 134 | 141 |
| Comparative Example 5 | 9.18 | 5.25 | 96 | 100 | 2.1 | 9.1 | 1.94 | 0.63 | 5.3 | 20.8 | 3.0 | 1.1 | 5.9 | 2.8 | 100 | 106 |
| Example 1 | 3.91 | 2.92 | 157 | 155 | 5.5 | 15.8 | 0.95 | 0.44 | 24.8 | 59.7 | 1.4 | 0.7 | 2.2 | 1.5 | 168 | 169 |
| Example 2 | 3.72 | 2.78 | 139 | 140 | 5.0 | 16.1 | 1.00 | 0.43 | 23.0 | 61.3 | 1.4 | 0.7 | 2.3 | 1.5 | 151 | 155 |
| Example 3 | 3.59 | 2.74 | 123 | 134 | 4.7 | 15.6 | 1.04 | 0.45 | 20.5 | 58.6 | 1.5 | 0.7 | 2.4 | 1.6 | 136 | 149 |
| Example 4 | 7.35 | 4.51 | 116 | 129 | 2.3 | 10.1 | 1.77 | 0.61 | 6.1 | 27.4 | 2.6 | 1.0 | 4.4 | 2.2 | 122 | 141 |
| Example 5 | 4.35 | 3.32 | 144 | 146 | 4.2 | 11.9 | 1.10 | 0.54 | 16.3 | 39.5 | 1.6 | 0.9 | 2.6 | 1.8 | 158 | 158 |
| Example 6 | 5.37 | 3.87 | 150 | 148 | 3.3 | 11.0 | 1.29 | 0.58 | 11.7 | 33.5 | 1.9 | 0.9 | 3.0 | 2.0 | 160 | 163 |
| Example 7 | 6.26 | 4.35 | 147 | 155 | 2.9 | 10.3 | 1.42 | 0.61 | 9.2 | 29.9 | 2.1 | 1.0 | 3.4 | 2.1 | 154 | 165 |
| Example 8 | 7.30 | 4.50 | 148 | 142 | 2.5 | 9.8 | 1.62 | 0.63 | 7.3 | 27.9 | 2.4 | 1.0 | 3.9 | 2.2 | 153 | 154 |
| Example 9 | 4.98 | 3.79 | 174 | 177 | 4.0 | 10.4 | 1.13 | 0.62 | 14.8 | 35.1 | 1.7 | 1.0 | 2.7 | 1.9 | 191 | 192 |
| CD ROD BONDING PATTERN |||||||||||||||||
| Comparative Example 6 | 3.4 | 2.3 | 177 | 180 | 14.1 | 41.1 | 0.5 | 0.1 | 62.1 | 132.6 | 0.8 | 0.3 | 1.5 | 0.8 | 194 | 202 |
| Comparative Example 7 | 3.4 | 2.6 | 213 | 222 | 13.4 | 32.7 | 0.6 | 0.2 | 71.4 | 119.1 | 0.9 | 0.4 | 1.5 | 1.0 | 234 | 248 |
| Comparative Example 8 | 3.5 | 2.6 | 186 | 185 | 13.5 | 34.0 | 0.5 | 0.2 | 58.5 | 106.2 | 0.8 | 0.3 | 1.6 | 1.0 | 203 | 210 |
| Comparative Example 9 | 4.0 | 2.8 | 184 | 194 | 10.4 | 32.5 | 0.6 | 0.2 | 44.1 | 98.0 | 1.0 | 0.3 | 1.8 | 1.0 | 204 | 220 |
| Comparative Example 10 | 4.8 | 3.4 | 181 | 182 | 8.7 | 25.5 | 0.7 | 0.2 | 30.4 | 65.3 | 1.1 | 0.4 | 2.1 | 1.2 | 195 | 197 |
| Comparative Example 11 | 5.6 | 3.8 | 166 | 169 | 7.0 | 23.1 | 0.8 | 0.2 | 21.9 | 53.2 | 1.3 | 0.4 | 2.5 | 1.4 | 178 | 188 |
| Comparative Example 12 | 6.8 | 4.4 | 161 | 159 | 5.2 | 19.9 | 1.0 | 0.3 | 15.2 | 42.7 | 1.6 | 0.5 | 3.1 | 1.6 | 173 | 176 |
| Comparative Example 13 | 3.5 | 2.5 | 178 | 182 | 13.2 | 34.6 | 0.6 | 0.2 | 56.8 | 109.9 | 0.9 | 0.3 | 1.6 | 1.0 | 198 | 205 |
| Comparative Example 14 | 4.0 | 3.0 | 186 | 199 | 10.6 | 28.2 | 0.6 | 0.2 | 43.6 | 82.1 | 1.0 | 0.4 | 1.8 | 1.1 | 210 | 223 |
| Comparative Example 15 | 7.2 | 3.9 | 117 | 109 | 3.8 | 19.3 | 1.2 | 0.3 | 10.6 | 39.1 | 1.9 | 0.5 | 4.0 | 1.7 | 125 | 120 |

TABLE 10-continued

| | | | | | | | MDT at 5% N/cm | CDT at 5% N/cm | | | MDT at 10% N/cm | CDT at 10% N/cm | MDT at 33% N/cm | CDT at 33% N/cm | Break-point % | Break-point % |
|---|---|---|---|---|---|---|---|---|---|---|---|---|---|---|---|---|
| Sample ID No. | MDT N/cm | CDT N/cm | MDE % | CDE % | MDE at 5N % | CDE at 5N % | | | MDE at 10N % | CDE at 10N % | | | | | | |

Tensile test at 100 mm/min

| Sample ID No. | MDT N/cm | CDT N/cm | MDE % | CDE % | MDE at 5N % | CDE at 5N % | MDT at 5% N/cm | CDT at 5% N/cm | MDE at 10N % | CDE at 10N % | MDT at 10% N/cm | CDT at 10% N/cm | MDT at 33% N/cm | CDT at 33% N/cm | Break-point % | Break-point % |
|---|---|---|---|---|---|---|---|---|---|---|---|---|---|---|---|---|
| Example 10 | 3.4 | 2.3 | 198 | 199 | 11.8 | 35.3 | 0.6 | 0.2 | 66.5 | 136.5 | 0.9 | 0.4 | 1.6 | 1.0 | 214 | 224 |
| Example 11 | 3.7 | 2.8 | 207 | 214 | 10.5 | 27.7 | 0.6 | 0.3 | 54.4 | 102.4 | 1.0 | 0.4 | 1.7 | 1.1 | 223 | 238 |
| Example 12 | 2.5 | 2.0 | 185 | 189 | 17.0 | 39.2 | 0.6 | 0.2 | 109.4 | 154.8 | 0.8 | 0.4 | 1.3 | 0.9 | 211 | 216 |
| Example 13 | 3.4 | 2.6 | 155 | 167 | 11.9 | 29.8 | 0.6 | 0.2 | 55.0 | 96.2 | 0.9 | 0.4 | 1.6 | .1 | 172 | 188 |
| Example 14 | 3.9 | 2.8 | 167 | 171 | 9.9 | 27.4 | 0.7 | 0.2 | 45.1 | 85.7 | 1.0 | 0.4 | 1.8 | .1 | 185 | 195 |
| Example 15 | 5.0 | 3.4 | 154 | 165 | 6.5 | 23.1 | 0.9 | 0.3 | 25.8 | 61.9 | 1.3 | 0.5 | 2.2 | .3 | 169 | 185 |
| Example 16 | 6.1 | 3.9 | 144 | 154 | 4.8 | 20.5 | 1.0 | 0.3 | 17.7 | 50.4 | 1.6 | 0.5 | 2.7 | .5 | 156 | 169 |
| Example 17 | 7.2 | 4.2 | 141 | 145 | 3.8 | 19.1 | 1.2 | 0.3 | 12.9 | 44.0 | 1.8 | 0.6 | 3.2 | .6 | 149 | 159 |
| Example 18 | 3.6 | 2.6 | 157 | 171 | 10.4 | 30.9 | 0.7 | 0.2 | 50.7 | 97.8 | 1.0 | 0.4 | 1.7 | 1.0 | 176 | 191 |
| Example 19 | 3.9 | 2.9 | 165 | 172 | 8.8 | 26.4 | 0.7 | 0.3 | 41.4 | 80.1 | 1.1 | 0.4 | 1.8 | 1.2 | 183 | 194 |
| Example 20 | 8.6 | 4.4 | 123 | 124 | 2.6 | 18.3 | 1.6 | 0.3 | 7.7 | 38.7 | 2.3 | 0.6 | 4.2 | 1.7 | 131 | 137 |
| Example 21 | 4.1 | 3.1 | 187 | 188 | 4.8 | 15.7 | 1.0 | 0.6 | 26.9 | 63.9 | 1.4 | 0.8 | 2.1 | 1.5 | 201 | 213 |

REVERSE BICOMPONENT INVENTIVE BLEND IN SHEATH/PE CORE

| Example 22 | 2.5 | 1.7 | 228 | 197 | 21.2 | 53.4 | 0.5 | 0.2 | 135.5 | 241.9 | 0.7 | 0.3 | 1.2 | 0.7 | 250 | 229 |
| Example 23 | 2.4 | 1.7 | 223 | 222 | 22.4 | 60.1 | 0.5 | 0.1 | 148.3 | | 0.7 | 0.3 | 1.2 | 0.7 | 248 | 260 |

REVERSE BICOMPONENT INVENTIVE BLEND IN SHEATH/ZIEGLER-NATTA PP CORE

| Example 24 | 5.7 | 4.1 | 129 | 121 | 3.8 | 10.4 | 1.19 | 0.56 | 12.7 | 28.2 | 1.8 | 1.0 | 3.1 | 2.2 | 140 | 133 |
| Example 25 | 5.7 | 4.1 | 120 | 115 | 3.8 | 10.9 | 1.18 | 0.55 | 12.5 | 28.4 | 1.8 | 0.9 | 3.2 | 2.2 | 129 | 127 |
| Example 26 | 5.3 | 4.1 | 137 | 139 | 4.1 | 11.2 | 1.12 | 0.55 | 14.8 | 31.6 | 1.7 | 0.9 | 2.9 | 2.1 | 147 | 153 |
| Example 27 | 5.6 | 4.3 | 117 | 131 | 3.8 | 10.9 | 1.18 | 0.55 | 12.5 | 28.8 | 1.8 | 0.9 | 3.2 | 2.2 | 130 | 142 |

REVERSE BICOMPONENT INVENTIVE BLEND IN SHEATH/PE CORE

| Example 28 | 2.9 | 2.3 | 148 | 149 | 8.5 | 22.6 | 0.71 | 0.28 | 42.7 | 94.7 | 1.1 | 0.5 | 1.8 | 1.3 | 162 | 167 |
| Example 29 | 2.9 | 2.2 | 145 | 139 | 8.9 | 22.4 | 0.69 | 0.29 | 42.9 | 98.4 | 1.1 | 0.5 | 1.8 | 1.3 | 167 | 162 |
| Example 30 | 3.0 | 2.4 | 156 | 159 | 8.8 | 20.9 | 0.70 | 0.34 | 43.9 | 93.5 | 1.1 | 0.6 | 1.8 | 1.3 | 166 | 174 |
| Example 31 | 2.4 | 1.9 | 88 | 91 | 7.8 | 21.7 | 0.78 | 0.32 | 40.4 | 100.1 | 1.1 | 0.6 | 1.9 | 1.3 | 103 | 114 |

HONEYCOMB BONDING PATTERN

| Comparative Example 26 | | | | | | | | | | | | | | | | |
| Comparative Example 27 | | | | | | | | | | | | | | | | |
| Comparative Example 28 | | | | | | | | | | | | | | | | |
| Comparative Example 29 | | | | | | | | | | | | | | | | |
| Comparative Example 30 | | | | | | | | | | | | | | | | |
| Comparative Example 31 | | | | | | | | | | | | | | | | |
| Example 32 | | | | | | | | | | | | | | | | |
| Example 33 | | | | | | | | | | | | | | | | |
| Example 34 | 4.5 | 3.5 | 157 | 171 | 5.5 | 14.9 | 1.0 | 0.4 | 20.2 | 53.3 | 1.4 | 0.8 | 2.4 | 1.6 | 170 | 184 |
| Example 35 | | | | | | | | | | | | | | | | |
| Example 36 | | | | | | | | | | | | | | | | |
| Example 37 | | | | | | | | | | | | | | | | |
| Example 38 | | | | | | | | | | | | | | | | |
| Example 39 | | | | | | | | | | | | | | | | |
| Example 40 | | | | | | | | | | | | | | | | |

REVERSE BICOMPONENT INVENTIVE BLEND IN SHEATH/ZIEGLER-NATTA PP CORE

| Example 41 | | | | | | | | | | | | | | | | |
| Example 42 | 2.7 | 2.0 | 156 | 182 | 10.5 | 32.5 | 0.7 | 0.2 | 59.6 | 156.4 | 1.0 | 0.4 | 1.7 | 1.0 | 178 | 198 |

TABLE 11

Neck-In

| Sample Identification No. | Neck-in material modulus N/m | Neck-in neckdown modulus N/m |
|---|---|---|
| Comparative Example 1 | | |
| Comparative Example 2 | 2141 | 381 |
| Comparative Example 3 | 2320 | 461 |
| Comparative Example 4 | | |

TABLE 11-continued

Neck-In

| Sample Identification No. | Neck-in material modulus N/m | Neck-in neckdown modulus N/m |
|---|---|---|
| Comparative Example 5 | | |
| Example 1 | | |
| Example 2 | 2317 | 405 |
| Example 3 | | |
| Example 4 | | |
| Example 5 | 3221 | 723 |
| Example 6 | | |
| Example 7 | 4087 | 989 |
| Example 8 | 4488 | 1180 |
| Example 9 | 3379 | 997 |
| Comparative Example 6 | | |
| Comparative Example 7 | | |
| Comparative Example 8 | | |
| Comparative Example 9 | 1278 | 247 |
| Comparative Example 10 | | |
| Comparative Example 11 | | |
| Comparative Example 12 | | |
| Comparative Example 13 | | |
| Comparative Example 14 | | |
| Comparative Example 15 | | |
| Example 10 | | |
| Example 11 | | |
| Example 12 | | |
| Example 13 | | |
| Example 14 | 1540 | 269 |
| Example 15 | | |
| Example 16 | | |
| Example 17 | | |
| Example 18 | | |
| Example 19 | | |
| Example 20 | | |
| Example 21 | | |
| Example 22 | | |
| Example 23 | 747 | 156 |
| Example 24 | | |
| Example 25 | | |
| Example 26 | 2918 | 638 |
| Example 27 | | |
| Example 28 | | |
| Example 29 | | |
| Example 30 | 1570 | 367 |
| Example 31 | | |
| Comparative Example 26 | | |
| Comparative Example 27 | | |
| Comparative Example 28 | | |
| Comparative Example 29 | | |
| Comparative Example 30 | | |
| Comparative Example 31 | | |
| Example 32 | | |
| Example 33 | | |
| Example 34 | | |
| Example 35 | | |
| Example 36 | | |
| Example 37 | | |
| Example 38 | | |
| Example 39 | | |
| Example 40 | | |
| Example 41 | | |
| Example 42 | | |

In Tables 13 and 14 below, additional trials were conducted to compare the differences in nonwoven fabrics comprising a blend of metallocene-catalyzed polypropylene, polyethylene, and a third polymer component (e.g., a polypropylene copolymer) in comparison to a blend comprising a Ziegler-Natta catalyzed propylene. The compositions of each sample are provided as follows in Table 12.

From Tables 13 and 14, it can be seen that the nonwoven fabrics in accordance with the present invention exhibited significantly improved elongations in both the machine and cross directions of the fabric. Accordingly, a metallocene-catalyzed polypropylene provides unexpected improvement in comparison to a blend comprising Ziegler-Natta catalyzed propylene.

TABLE 12

Sample Compositions

| | Sample Identification No. | | | |
|---|---|---|---|---|
| | Example 43 | Comparative Example 32 | Example 44 | Comparative Example 33 |
| Composition | 77.9% PP-3; 17.9% 3-PC; 4.2% PE-1 | 77.9% PP-5; 17.9% 3-PC; 4.2% PE-1 | 77.9% PP-3; 17.9% 3-PC; 4.2% PE-1 | 77.9% PP-5; 17.9% 3-PC; 4.2% PE-1 |

TABLE 13

Sample Properties

Basis Weight Target 25 gsm

Sample ID No.:

| | Example 43 | | | Comparative Example 32 | | |
|---|---|---|---|---|---|---|
| Set #: | 313052002 | | | 313051013 | | |
| Data | Average | Stdev | Count | Average | Stdev | Count |
| Caliper (mm) | 0.22 | 0.01 | 40 | 0.24 | 0.01 | 384 |
| Air Perm (cfm) | 538 | 28 | 40 | 566.54 | 42.53 | 384 |
| MDT@Peak10 (N/2 in) | 35.76 | 2.38 | 40 | 36.15 | 3 | 32 |
| MDE@Peak10 (%) | 151.33 | 15.44 | 40 | 116.5 | 10.81 | 32 |
| CDT@Peak10 (N/2 in) | 22.9 | 2.32 | 40 | 21.28 | 2.63 | 32 |
| CDE@Peak10 (%) | 146.17 | 19.61 | 40 | 117.64 | 17.75 | 32 |
| MDT@Peak13 (N/2 in) | 39.94 | 3.43 | 40 | 40.89 | 3.7 | 32 |
| MDE@Peak13 (%) | 253.26 | 19.33 | 40 | 196.62 | 15.32 | 32 |
| CDT@Peak13 (N/2 in) | 26.79 | 3.04 | 40 | 25 | 3.01 | 32 |
| CDE@Peak13 (%) | 270.03 | 32.27 | 40 | 193.77 | 22.43 | 32 |
| CDT@Peak2 (N/in) | 9.61 | 1.07 | 40 | 9.77 | 1.53 | 400 |
| CDE@Peak2 (%) | 113.91 | 20.37 | 40 | 109.71 | 21.22 | 400 |
| MDT@Peak2 (N/in) | 15.3 | 1.62 | 40 | 17.19 | 2.12 | 400 |
| MDE@Peak2 (%) | 124.09 | 18.11 | 40 | 112.37 | 15.38 | 399 |

TABLE 14

Sample Properties

Basis Weight Target 20 gsm
Sample ID No.:

| Data | Example 44 | | | Comparative Example 33 | | |
|---|---|---|---|---|---|---|
| Set #: | 313052001 | | | 312344045 | | |
| | Average | Stdev | Count | Average | Stdev | Count |
| Caliper (mm) | 0.19 | 0.01 | 40 | 0.2 | 0.01 | 408 |
| Air Perm (cfm) | 648 | 34 | 40 | 757 | 57.89 | 408 |
| MDT@Peak10 (N/2 in) | 29.49 | 2.79 | 40 | 33.79 | 3.02 | 32 |
| MDE@Peak10 (%) | 145.92 | 16.85 | 40 | 128.08 | 14.6 | 32 |
| CDT@Peak10 (N/2 in) | 17.03 | 2.23 | 40 | 16.89 | 2.24 | 32 |
| CDE@Peak10 (%) | 143.54 | 20.4 | 40 | 115.47 | 17.21 | 32 |
| MDT@Peak13 (N/2 in) | 34.34 | 2.89 | 40 | 21.22 | 2.98 | 32 |
| MDE@Peak13 (%) | 253.47 | 19.11 | 40 | 209.43 | 29.49 | 32 |
| CDT@Peak13 (N/2 in) | 20.44 | 2.65 | 40 | 37.5 | 3.46 | 32 |
| CDE@Peak13 (%) | 261.7 | 32.17 | 40 | 206.1 | 17.93 | 32 |
| CDT@Peak2 (N/in) | 7.21 | 1.02 | 40 | 7.32 | 1.11 | 493 |
| CDE@Peak2 (%) | 109.6 | 21.5 | 40 | 109.48 | 37.76 | 493 |
| MDT@Peak2 (N/in) | 13.13 | 1.29 | 40 | 14.27 | 1.76 | 456 |
| MDE@Peak2 (%) | 127.96 | 14.86 | 40 | 107.97 | 16.32 | 456 |

Values for Peak10 were determined using TEST 10.
Values for Peak 2 were determined using TEST 2.

TABLE 15

Comparison of Inventive Fabrics with Prior Art

| Sample Identification | Maximum Force (Normalized in Nm²/g-cm) | Elongation at Maximum Force as % | Maximum Elongation at Break as % | Elongation at 30% reduction in Stain after peak | Strain Deterioration Rate (At 30% Stain Loss) | Nonwoven Toughness N-m(2)/gram (Area under the Stress Stain Curve) |
|---|---|---|---|---|---|---|
| Example 6 | 0.275 | 330 | 700 | 475 | 8.1 × 10(−2) | 50.8 × 10(−2) |
| Comparative Example 6 | 0.22 | 340 | 700 | 405 | 6.3 × 10(−2) | 38.5 × 10(−2) |
| Example 44 | 0.22 | 260 | 600 | 380 | 6.4 × 10(−2) | 36.3 × 10(−2) |
| Comparative Example 33 | 0.16 | 200 | 600 | 320 | 3.8 × 10(−2) | 25.1 × 10(−2) |
| Comparative Example 10 | 0.16 | 300 | 800 | 440 | 2.7 × 10(−2) | 32.0 × 10(−2) |
| Example 15 | 0.16 | 430 | 850 | 540 | 3.7 × 10(−2) | 37.7 × 10(−2) |
| Example 23 | 0.11 | 480 | 1120 | 620 | 1.7 × 10(−2) | 32.6 × 10(−2) |
| HEC* | 0.055 | 220 | 800 | 320 | 1.9 × 10(−2) | 9.66 × 10(−2) |
| VHEC** | 0.03 | 200 | 800 | 520 | 0.49 × 10(−2) | 6.65 × 10(−2) |
| SSMMS*** | 0.13 | 270 | 700 | 380 | 4.1 × 10(−2) | 28.1 × 10(−2) |
| SSMMS*[1] | 18.5 | 180 | 500 | 340 | 4.0 × 10(−2) | 31.3 × 10(−2) |
| SMMS*[2] | 22 | 100 | 330 | 190 | 10.6 × 10(−2) | 19.1 × 10(−2) |
| HEC*[3] | 0.066 | 250 | 900 | 390 | 1.4 × 10(−2) | 14.8 × 10(−2) |

*Commercially available Carded thermally bonded polypropylene nonwoven.
**Commercially available Carded thermally bonded polypropylene nonwoven.
***Example IV of U.S. Pat. No. 8,226,626 (where S = BICO PE/PP).
*[1]Example III of U.S. Pat. No. 8,226,626 (where S = BICO PE/PP).
*[2]Example II of U.S. Pat. No. 8,226,626 (where S = PP).
*[3]Example I of U.S. Pat. No. 8,226,626, carded nonwoven web available from Albis Germany Nonwoven GmbH.

Discussion of Table 15

From Table 15 it can be seen that the nonwovens prepared from the inventive polymer blend exhibit both improved elongations, strain deterioration and toughness in comparison to nonwovens comprising the Zeigler-Natta catalyzed propylene. This result is surprising and unexpected. In particular, the inventive nonwovens show 20-30% higher toughness in comparison to the nonwovens prepared from a blend comprising Zeigler-Natta catalyzed propylene.

Surfactant Treated Bicomponent Fabric

In this example, two bicomponent nonwoven fabrics (Examples 45 and 46) were prepared having a sheath/core configuration. The fabrics were made in a similar as Example 23, see Table 6 above, with the exception that the sheath was 100% PE and the core comprised 76% PP-2; 20% 3-PC; and 4% PE. Following extrusion the fibers were drawn and laid down on a collection surface, and then calendered bonded using a calender roll having a CD-rod bond pattern. Temperatures of the calender roll were reduced to reflect the bonding temperature of the PE sheath.

Example 45 was treated with a hydrophilic surfactant (Stantex 6327 available from Pulcra Chemicals LLC of Rock Hill, S.C.). The surfactant was applied with a kiss roll treatment followed by passing the treated nonwoven through a drying oven. Surfactant uptake was about 0.6 wt. % based on the total weight of the nonwoven fabric. The properties of the nonwoven fabrics of Examples 45 and 46 are summarized in Table 16 below.

TABLE 16

Properties of surfactant treated nonwoven fabric

| Nonwoven Fabric Properties | Test Method | Units | Bond Pattern | Example 45 | Example 46 |
|---|---|---|---|---|---|
| Basis weight | WSP 130.1 | (GSM) | CD-Rod | 19.4 | 20.7 |
| Peak Force CD | TM-1 | (N/gsm) | CD-Rod | 0.07 | 0.06 |
| Peak Elongation CD | TM-1 | (%) | CD-Rod | 233 | 217 |

TABLE 16-continued

Properties of surfactant treated nonwoven fabric

| Nonwoven Fabric Properties | Test Method | Units | Bond Pattern | Example 45 | Example 46 |
|---|---|---|---|---|---|
| Break Point CD | TM-1 | (%) | CD-Rod | 1160 | 1094 |
| Peak Force MD | TM-2 | (N/cm) | CD-Rod | 3.6 | 4.1 |
| Peak Elongation CD | TM-2 | (%) | CD-Rod | 218 | 211 |
| Peak Force MD | TM-2 | (N/cm) | CD-Rod | 1.5 | 1.3 |
| Peak Elongation CD | TM-2 | (%) | CD-Rod | 175 | 171 |

Basis weights for Examples 45 and 46 were determined with Test method WSP 130.1.
Peak Force CD, Peak Elongation CD, and Break Point CD were evaluated by TM-1 via the Pre-activation Test described in Turner et al. in U.S. Pat. No. 8,231,595 at a crosshead speed of 120 mm/min, initial distance between clamps of 5 mm, and sample width of 10 mm.
Peak Force and Peak Elongation both MD and CD were determined via EDANA method 20.2-89 at a cross head speed of 100 mm/min, initial distance between the clamps of 100 mm, and sample width of 50 mm.

The hydrophilic nature of Example 45 was demonstrated by measuring the Strike Through rate for passage of synthetic urine through the fabric by generally following the method of EDANA WSP 70.3 (08); single gush, 5 ml synthetic urine, 5 layers of filter paper. Example 45 showed values of 3.8 seconds (embossed side) and 4.8 seconds (smooth side) thus suggesting utility as a topsheet for as example baby diapers or adult incontinence products.

Simulated SMS (Example 21)

A simulated SMS fabric was made comprising a spunbond layer comprising filaments comprising a blend of metallocene catalyzed polypropylene, polyethylene, and a third polymer component (e.g., a polypropylene copolymer) (See nonwoven fabric of Example 21) and a meltblown layer comprising meltblown fibers comprising the propylene melt blown grade resin (MFR 800) commercially available from Borealis. The spunbond layer had a basis layer 18 g/m² and the meltblown layer had a basis weight of 2 g/m². The total basis weight for the SM fabric was 20 g/m². The fabric was made on a Reicofil-3 line in bico configuration. This makes the use of two independent extruders necessary, one for the core and the other for the sheath of the fiber. The technical details are known to someone skilled in the art. The overall process comprises the steps of:

extrusion melting of a thermoplastic polymer or a blend of thermoplastic polymers
pressing the melt through orifices to form fibers
quenching the fibers with cold air
stretching the fibers with accelerated air
lay-down of the fibers on a porous carrier sheet
transporting the unconsolidated fiber mat to a consolidation unit, most often a calender
bonding the mat to form a nonwoven fabric, and
winding the fabric.

The extruders can be feed with either the same polymer or with different polymers for the core and the sheath. The process temperatures that have to be used strongly depend on the melting points of the polymers and their viscosities. The melt was pressed through orifices to shape the overall geometry of the fiber. In general round fiber cross-sections are most common, but many other cross-section such as, e.g. tri- or multilobal, oval and flat, to name a few, are also possible.

The fibers then passed through a quench zone for cooling and crystallization of the polymer. The quench is done with cold air, most often around or below room temperature. Quench air and filaments then enter the acceleration zone, where the filaments are drawn and stretched to their final diameter, which usually is between 10-25 μm. The stretched fibers are then collected and spread on a forming wire as a loose fiber mat. Consolidation of the fibers to form a spunbond fabric can be done in various ways, e.g. by thermal calendering, ultrasonic bonding, needle punching, hydroentanglement, and many other methods known to someone skilled in the art.

A very convenient way of web consolidation is done by thermal calendering. In that process, the unconsolidated fabric is passed through two heated rollers, one of them with a smooth surface and the other with a 3-dimensional geometric pattern. This pattern can be made up of points, ellipses, lines and many other possible figures. The task is to press the filaments together at certain defined regions, partially melt them and thereby gluing them together. It is easily understandable that the bond pattern in use has a dramatic impact on the resulting physical fabric properties, and care has to be taken in regard of size and density of the bonded areas, as well as on the total consolidated area.

For specific application a spunbond fabric can be too porous and too permeable, so that often a second layer of finer fibers is added on top of the spunbond layer. These finer fibers result from a melt blown process, in which a highly flowable polymer is extruded through small orifices to form a thin melt string. Hot air is then blown towards these melt strings with high speed, thereby accelerating them and drawing them into fibers with diameters in the average below 5 μm. The thus formed SM-fabric (spunbond-meltblown) passes through the calender and is consolidated.

Preparation of Spunbond/Meltblown/Spunbond/Meltblown (SMMS) Fabric

Several SMMS fabrics were prepared which included spunbond nonwoven webs that are in accordance with the present invention. The SMMS fabrics were prepared on a commercial Recofil R-4 SMMS machine (spunbond beam+meltblown beam+meltblown beam+spunbond beam) as currently offered for sale by the Reifenhauser Company Machinenfabrik in Troisdorf, Germany (see, e.g., U.S. Pat. Nos. 5,162,074; 5,344,297; 5,466,410; 5,814,349, and 6,908,292). The bonding calender consisted of a smooth roll and an embossed roll where the embossed pattern consisted of oval elliptical pattern of approximately 18% bond area, which is well known to those skilled in the Recofil spunbond art.

The spunbond layers of the SMMS fabrics were prepared with the following composition: 75.25% PP-3; 20% 3-PC; 4.5% PE-1: and 0.25 $TiO_2$ as a colorant.

The polymer blend used to spin the fibers comprising the spunbond layers of the SMMS were prepared as described below. The polymeric components were added via the standard R-4 dosing units. Extra care was used in adding the slightly "sticky" Adflex component. The R-4 SMMS machine was operated following normal procedures as recommended by Recofil to produce low basis weight hygiene products and understood by those skilled in the art except as noted below. Purge-in and start-up of the spunbond (SB) beams went smoothly with no significant drips. The draw force as reflected in the cabin pressure was reduced to provide lower draw than typically utilized for hygiene polypropylene (PP) spunbond production as noted by the elevated spunbond fiber deniers reported in Table 17 and 18 below. The calender temperature was also reduced compared to typical PP conditions to reflect lower melt temperature of the polymer blend versus 100% polypropylene.

Example 47 was made at slightly higher cabin pressure and calender temperature than Example 48 as reflected in slightly lower fiber denier and slightly higher tensile seen in Example 47. The nonwoven fabric of Example 49 was made at the same cabin pressure as Example 48, but with a 5 degree C. reduction in calender oil temperature. Example 50 was made at the same cabin pressure and calender oil temperature as Example 49 but the machine wire speed was increased to yield the significant reduction in basis weight noted in Table 17. The spunbond fabric properties for Examples 47-50 are set forth in Table 17 below.

ture was increased by 5 degrees C. The SMMS of Example 3 was made with no change in spunbond spinning conditions or calender oil temperature but by adjusting line speed and meltblown through-put to target a spunbond basis weight of 12 GSM and a meltblown basis weight of 2 GSM.

TABLE 17

Spunbond Nonwoven Properties for Examples 47-50

Figure 11:
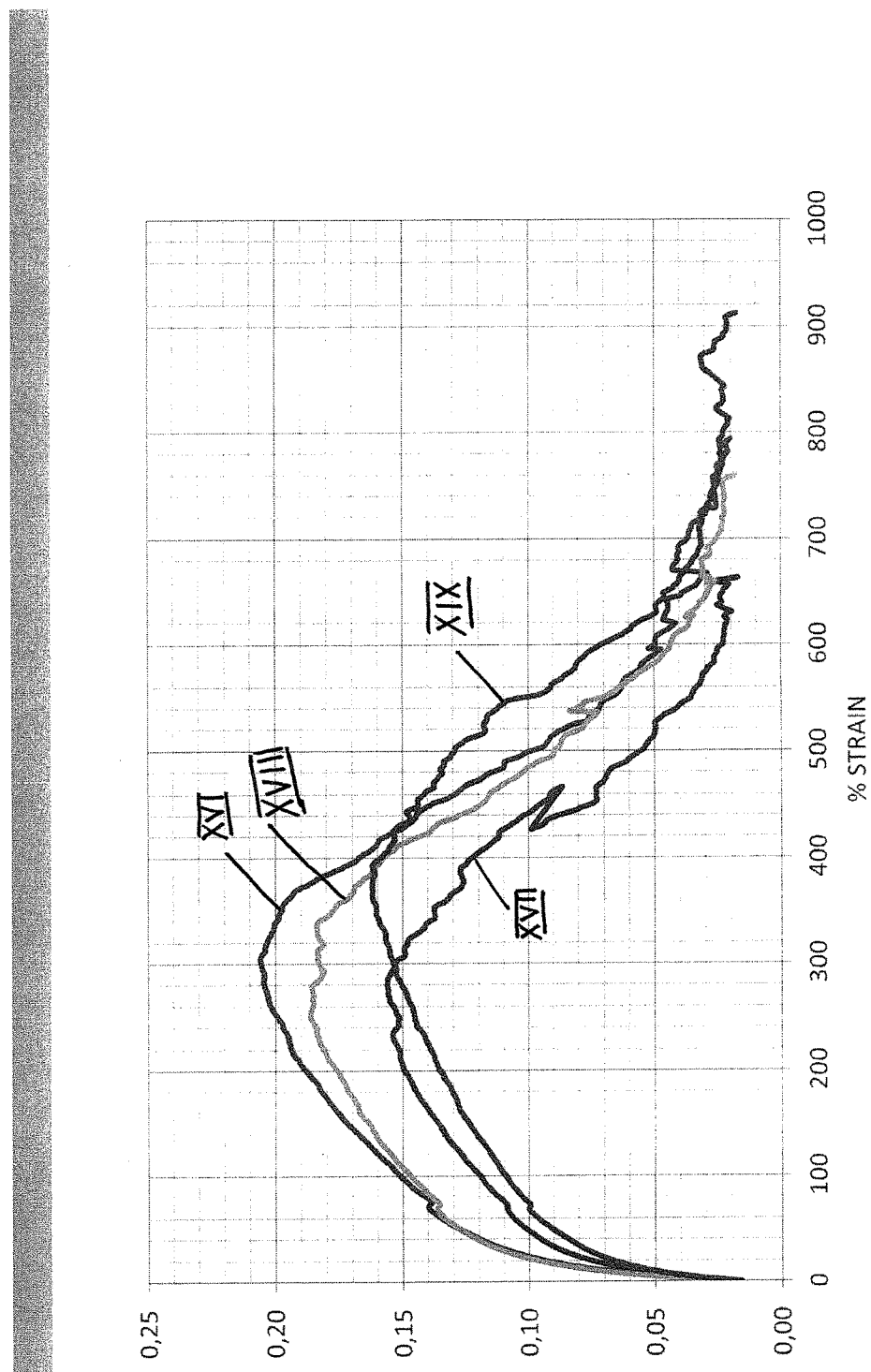

| Nonwoven Properties Properties slit rolls | Unit | Example 47 1 | Example 48 2 | Example 49 3 | Example 50 4 |
|---|---|---|---|---|---|
| Basis weight | gsm | 18.9 | 18.9 | 19.0 | 12.7 |
| Filament denier | dpf | 2.2 | 2.3 | 2.4 | 2.6 |
| Air perm | cfm | 772 | 891 | 911 | 1.314 |
| Peak strength MD | N/in | 10.3 | 8.5 | 9.7 | 8.0 |
| Peak strength CD | N/in | 6.9 | 5.7 | 5.8 | 3.1 |
| Peak elongation MD | % | 125 | 120 | 147 | 156 |
| Peak elongation CD | % | 120 | 116 | 117 | 132 |
| Normalized force MD | Nm$^2$/gcm | 0.29 | 0.29 | 0.27 | 0.28 |
| Normalized force CD | Nm$^2$/gcm | 0.21 | 0.16 | 0.20 | 0.17 |
| Peak elongation MD | % | 285 | 291 | 316 | 361 |
| Peak elongation CD | % | 311 | 290 | 300 | 387 |
| Breakpoint MD | % | 614 | 633 | 702 | 743 |
| Breakpoint CD | % | 678 | 643 | 672 | 820 |
| Roman Numeral ID for Example in FIG. 11 | — | XVI | XVII | XVIII | XIX |

Basis weight shown in Table 17 was determined following Test method WSP 130.1.
Tensile strength, CD peak; Elongation, CD Peak; and Tensile strength, CD at 33% were determined according to EDANA method 20.2-89 with cross head speed of 100 mm/min, initial distance between the clamps of 100 mm, and sample width of 50 mm.
Results for Normalized force, CD peak; Elongation CD-peak; and Breakpoint, CD; were determined via the Pre-activation Test suggested by Turner et al. in U.S. Pat. No. 8,231,595 with crosshead speed of 120 min/min, initial distance between clamps of 5 mm, and sample width of 10 mm.
The Air perm (Air Permeability) was determined with a sample area of 38 cm2 and air pressure of 125 Pa.

Following production of the spunbond fabrics of Examples 47-50, the line was then shut down with spinning continuing in drool mode while the two meltblown beams were prepared for operation. The meltblowing beams were operated in typical polypropylene mode using 100% meltblowing grade polypropylene resin H155 PP, available from Braskem in Brazil. The polymer blend of the instant invention was not used as the resin for meltblowing. When the meltblowing beams were ready the trial resumed now in the SMMS mode.

Example 51 was made with spunbond spinning conditions including cabin pressure set as used for candidate 49. Note, however, that spunbond conditions were not perfectly reproduced during SMMS candidate production since observed spunbond fiber deniers are in all cases higher during SMMS versus spunbond production. As understood by those skilled in the operation of Recofil R-4 SMMS machines, the wire speed was increased and the meltblown thru-put adjusted to target 2 grams per square meter (GSM) meltblown and 18 GSM spunbond basis weight. The calender oil temperature was set 5 degrees C. lower than the setting used in Example 49 above.

The SMMS of Example 52 was made at the same conditions as Example 51 except that the calender oil tempera- Example 54 resulted from reducing line speed and meltblown thru-put such that spunbond basis weight of 19.4 GSM and meltblown basis weight of 0.6 GSM was targeted. For Example 54 the calender oil temperature was increased 5 degrees C. versus Example 53 and the draw force as measured by cabin pressure was increased to equal that used in Example 47. For Example 55 the line speed and meltblown through-put was adjusted to target a spunbond basis weight of 18 GSM and a meltblown basis weight of 2 GSM. Both calender oil temperature and cabin pressure remained as targeted in Example 54. Example 56 was produced under similar conditions as Example 55 except that the cabin pressure was reduced to equal that used in candidate 2. Table 18 summarizes the properties of the SMMS fabrics prepared using a spundbond layer in accordance with embodiments of the invention. Table 18 summarizes observed properties of the SMMS of Examples 51 to 56. Results were obtained by the test methods summarized in Table 17. Mechanical properties are generally similar to those observed for the spunbond examples in Table 17. Thus, the spunbond layer of the SMMS structure primarily determines extensibility of the resulting SMMS product. It is noted, however, that the significant reduction in Air Permeability for the SMMS examples demonstrate the barrier properties provided by the low basis weight additions of meltblown fibers.

TABLE 18

SMMS Properties for Examples 47-50

| SMMS Properties | Unit | Example 51 | Example 52 | Example 53 | Example 54 | Example 55 | Example 56 |
|---|---|---|---|---|---|---|---|
| Basis weight | gsm | 19.6 | 19.7 | 13.0 | 19.6 | 19.5 | 19.4 |
| Filament denier | dpf | 2.9 | 3.3 | 3.4 | 3.1 | 2.6 | 2.5 |
| Air perm | cfm | 151 | 144 | 211 | 241 | 154 | 149 |
| Peak strength MD | N/in | 9.0 | 9.6 | 6.8 | 11.1 | 10.2 | 9.6 |

TABLE 18-continued

SMMS Properties for Examples 47-50

Figure 12:
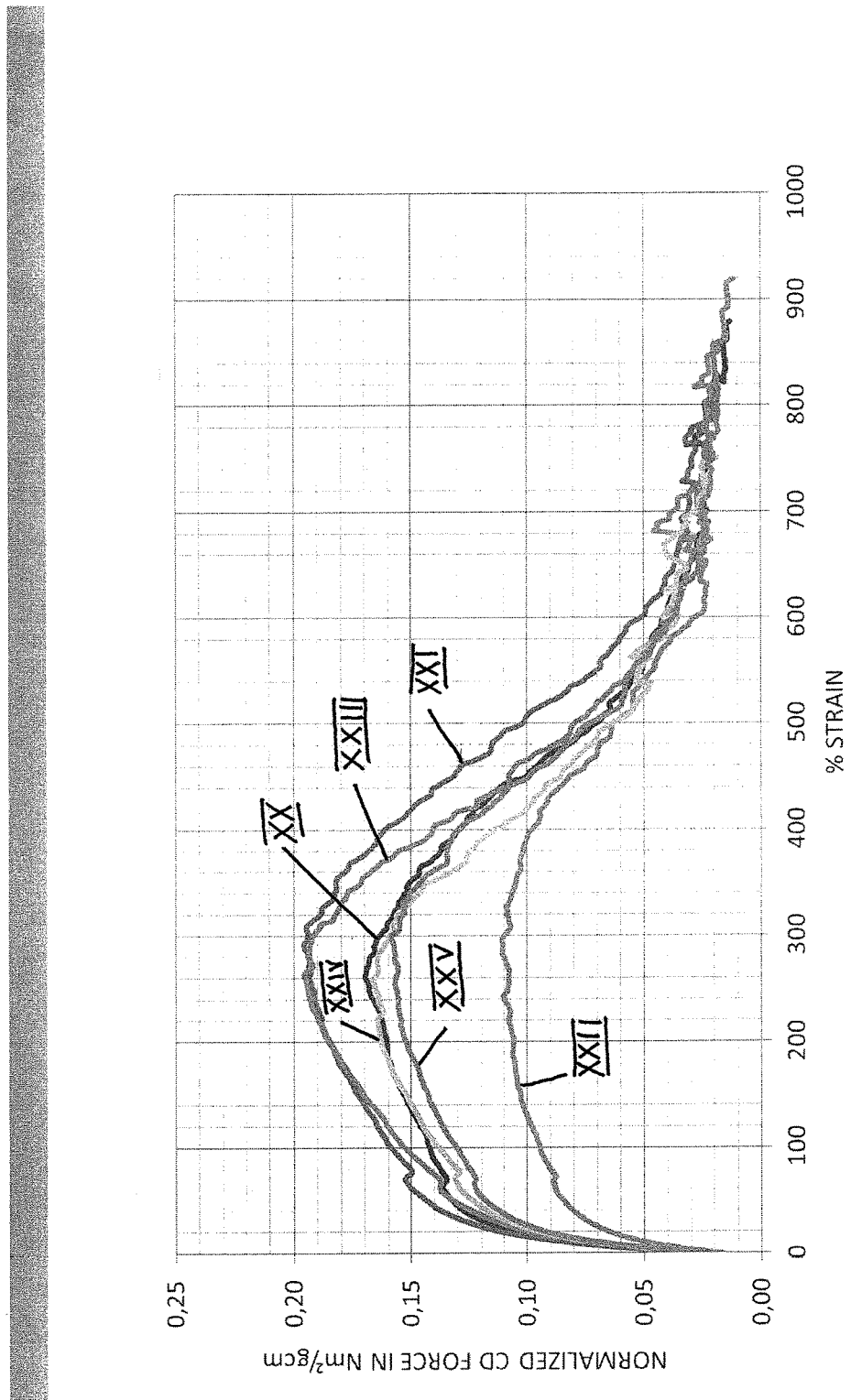

| SMMS Properties | Unit | Example 51 | Example 52 | Example 53 | Example 54 | Example 55 | Example 56 |
|---|---|---|---|---|---|---|---|
| Peak strength CD | N/in | 6.1 | 6.2 | 2.7 | 7.0 | 6.8 | 5.7 |
| Peak elongation MD | % | 128 | 135 | 129 | 130 | 114 | 135 |
| Peak elongation CD | % | 117 | 114 | 93 | 114 | 119 | 110 |
| Normalized force MD | Nm²/gcm | 0.28 | 0.24 | 0.29 | 0.30 | 0.28 | 0.20 |
| Normalized force CD | Nm²/gcm | 0.17 | 0.20 | 0.12 | 0.20 | 0.17 | 0.16 |
| Peak elongation MD | % | 293 | 253 | 300 | 293 | 286 | 263 |
| Peak elongation CD | % | 283 | 286 | 284 | 273 | 248 | 304 |
| Breakpoint MD | % | 665 | 682 | 701 | 631 | 593 | 682 |
| Breakpoint CD | % | 760 | 750 | 753 | 669 | 624 | 730 |
| Roman Numeral ID for Example in FIG. 12 | — | XX | XXI | XXII | XXIII | XXIV | XXV |

FIG. 11 is a chart that illustrates a CD Stress/Strain curves for Examples 47-50 of Table 17 as determined by the Pre-Activation test described previously (see, for example, Turner et al.; U.S. Pat. No. 8,231,595). The Pre-Activation test evaluates the stretching behavior of a single layer of nonwoven. Easy to activate (stretch via ring rolling) nonwoven fabrics show low stretching force in combination with high extensibility. The area under the stress/strain curve suggests toughness, the capability of the activated nonwoven to provide force resistance after activation. From FIG. 11 it can be seen that the spunbond nonwovens of Examples 47-48 show the highly desirable and contrary properties of both high extensibility at low force and thus ease of activation yet toughness after activation so the resulting nonwoven can provide strength to the component of some article such as a diaper ear or a side-panel of a diaper pant after activation.

FIG. 12 shows CD Stress/Strain curves for Examples 51-56 of Table 18 as determined by the Pre-Activation test. As noted above, addition of the meltblown fibers in the SMMS structure exhibited only a minor effect on the extensibility versus that seen for the Spunbond examples. Thus, the SMMS products promise particular utility for use in Ear or Side-Panel applications where the nonwoven must be adhesive laminated to elastic film and then stretched, for example via ring rolling, to provide elastic fit of the diaper or pant to the wearer, i.e. baby or incontinent adult. The barrier of the meltblown layer reduces propensity for glue bleed-through while preserving both ease of activation and retention of strength and toughness.

Modifications of the invention set forth herein will come to mind to one skilled in the art to which the invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A nonwoven fabric comprising a plurality of fibers that are bonded to each other together to form a coherent web, wherein the fibers are bonded to each other with a plurality of bond patterns consisting of cross-direction cylindrical or rod shaped bonds that extend only in the cross direction (CD) of the web.

2. The fabric of claim 1, wherein the fabric exhibits one or more of:

an increase in High Speed Deformation Simulation machine direction elongation at 5 N that is from about 25 to 150% in comparison to a similar fabric that has been thermally bonded with an oval shaped bond pattern;

an increase in High Speed Deformation Simulation cross direction elongation at 5 N that is from about 75 to 100% in comparison to a similar fabric that has been thermally bonded with an oval shaped bond pattern;

an increase in High Speed Deformation Simulation machine direction elongation at 10 N that is from about 75 to 125% in comparison to a similar fabric that has been thermally bonded with an oval shaped bond pattern; and an increase in High Speed Deformation Simulation cross direction elongation at 10 N that is from about 25 to 70% in comparison to a similar fabric that has been thermally bonded with an oval shaped bond pattern.

3. The fabric of claim 1, wherein the bonds cover from 8 to 12% of the fabric.

4. The fabric of claim 1, wherein the cross-directional cylindrical or rod shaped bond patterns have a length that is from about 1.5 to 10 times the width.

5. The fabric of claim 1, wherein the cross-directional cylindrical or rod shaped bond patterns have an aspect ratio defined by a length of the bond pattern divided by the width of the bond pattern that is from about 2 to 10.

6. The fabric of claim 5, wherein the aspect ratio of the bond patterns is from about 4 to 8.

7. The fabric of claim 1, wherein the fabric comprises a spunbond nonwoven fabric.

8. A composite sheet material having a plurality of layers defining a spunbond-meltblown-spunbond (SMS) construction in which the spunbond layer comprises the nonwoven fabric of claim 1.

9. A composite sheet material having a plurality of layers defining a spunbond-meltblown-meltblown-spunbond (SMMS) construction in which at least one of the spunbond layers comprises the nonwoven fabric of claim 1.

10. An absorbent article comprising the fabric of claim 1.

11. The absorbent article of claim 10, wherein the article comprises a diaper.

* * * * *